(12) United States Patent
Galley et al.

(10) Patent No.: US 7,858,652 B2
(45) Date of Patent: Dec. 28, 2010

(54) SUBSTITUTED 4-IMIDAZOLES

(75) Inventors: Guido Galley, Rheinfelden (DE); Katrin Groebke Zbinden, Liestal (CH); Roger Norcross, Olsberg (CH); Henri Stalder, Basel (CH)

(73) Assignee: Hoffmann-La Roche Inc., Nutley, NJ (US)

( * ) Notice: Subject to any disclaimer, the term of this patent is extended or adjusted under 35 U.S.C. 154(b) by 379 days.

(21) Appl. No.: 11/938,801

(22) Filed: Nov. 13, 2007

(65) Prior Publication Data
US 2008/0139533 A1    Jun. 12, 2008

(30) Foreign Application Priority Data
Nov. 16, 2006   (EP)   ................... 06124182

(51) Int. Cl.
- A61K 31/427 (2006.01)
- A61K 31/47 (2006.01)
- C07D 403/06 (2006.01)
- C07D 215/02 (2006.01)

(52) U.S. Cl. ................. 514/397; 548/311.1; 548/311.4; 548/312.1; 546/112; 546/152; 514/299; 514/311; 514/385

(58) Field of Classification Search ............... 548/300.1, 548/311.1, 312.1; 546/112, 152; 514/299, 514/311, 385, 396, 397
See application file for complete search history.

(56) References Cited

U.S. PATENT DOCUMENTS

| | | |
|---|---|---|
| 2,161,938 A | 6/1939 | Sonn |
| 2,457,047 A | 12/1948 | Kyrides |
| 2,731,471 A | 1/1956 | Synerholm et al. |
| 2,744,909 A | 5/1956 | Speeter |
| 2,744,910 A | 5/1956 | Speeter |
| 2,778,836 A | 1/1957 | Morren |
| 2,919,274 A | 12/1959 | Faust et al. |
| 3,161,653 A | 12/1964 | Fruhstorfer et al. |
| 3,354,175 A | 11/1967 | Fruhstorfer et al. |
| 3,377,247 A | 4/1968 | Elbe |
| 3,586,695 A | 6/1971 | Wysong et al. |
| 3,622,579 A | 11/1971 | Stahle et al. |
| 3,660,423 A | 5/1972 | Wysong et al. |
| 3,758,476 A | 9/1973 | Rippel et al. |
| 3,818,035 A | 6/1974 | Binon et al. |

(Continued)

FOREIGN PATENT DOCUMENTS

| | | |
|---|---|---|
| CA | 2246027 | 2/2000 |
| EP | 0 024 829 | 3/1981 |
| EP | 0 125 410 | 11/1984 |
| EP | 0 166 937 | 1/1986 |
| EP | 0 289 365 | 11/1988 |
| EP | 0 331 374 | 9/1989 |
| EP | 0 424 059 | 4/1991 |
| EP | 0 857 483 | 8/1998 |
| EP | 0 924 209 | 6/1999 |
| EP | 1 103 243 | 5/2001 |

(Continued)

OTHER PUBLICATIONS

Heidelbaugh et al (2006): STN International HCAPLUS database, (Columbus, Ohio), Accession number: 2006:299467.*

(Continued)

Primary Examiner—Golam M Shameem
(74) Attorney, Agent, or Firm—George W. Johnston; Patricia S. Rocha-Tramaloni; Kimberly J. Prior

(57) ABSTRACT

The present invention relates to a compound of formula I,

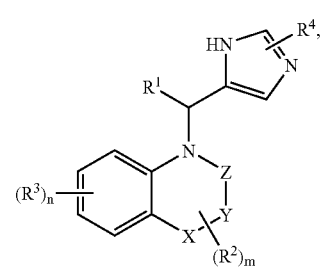

wherein
$R^1$ is selected from the group consisting of hydrogen and lower alkyl;
each $R^2$ is independently selected from the group consisting of hydrogen and lower alkyl;
each $R^3$ is independently selected from the group consisting of hydrogen, lower alkyl, lower alkoxy, phenyloxy, benzyloxy, halogen and lower alkyl substituted by halogen;
$R^4$ is selected from the group consisting of hydrogen and lower alkyl;
X is selected from the group consisting of —$CH_2$—, —CH— and —O—;
Y is selected from the group consisting of —$CH_2$—, —$CH_2CH_2$—, —CH— and a bond; with the proviso that, when X is —O—, Y is —$CH_2$—;
Z is selected from the group consisting of —$CH_2$— and —CH—;
m is 1 or 2; and
n is 1 or 2.

The invention relates also to a pharmaceutically-acceptable acid-addition salt of such a compound, methods for making the compound, and a composition comprising such a compound.

It has been found that the compounds of formula I have a good affinity to the trace amine associated receptors (TAARs), especially for TAAR1.

12 Claims, No Drawings

U.S. PATENT DOCUMENTS

| | | | |
|---|---|---|---|
| 3,818,094 | A | 6/1974 | Stahle et al. |
| 3,992,403 | A | 11/1976 | Roebke |
| 4,125,620 | A | 11/1978 | Stahle et al. |
| 4,146,647 | A | 3/1979 | Lafon |
| 4,323,570 | A | 4/1982 | Stenzel et al. |
| 4,665,095 | A | 5/1987 | Winn et al. |
| 4,962,200 | A * | 10/1990 | Kihara et al. ............... 544/333 |
| 5,610,174 | A | 3/1997 | Craig et al. |
| 5,658,938 | A | 8/1997 | Geerts et al. |
| 6,387,926 | B1 * | 5/2002 | Bhide et al. ................. 514/311 |
| 6,602,883 | B1 * | 8/2003 | Bhide et al. ................. 514/311 |
| 7,399,868 | B2 * | 7/2008 | Heidelbaugh et al. .... 548/311.1 |
| 2002/0019390 | A1 | 2/2002 | Wong et al. |
| 2003/0181354 | A1 | 9/2003 | Abdulrazik |
| 2003/0236274 | A1 | 12/2003 | Tasaka et al. |

FOREIGN PATENT DOCUMENTS

| | | |
|---|---|---|
| EP | 1 413 576 | 4/2004 |
| ES | 323 985 | 12/1966 |
| FR | 6 551 | 12/1968 |
| GB | 877306 | 9/1961 |
| GB | 1016514 | 1/1966 |
| WO | WO 96/22768 | 8/1996 |
| WO | WO 97/12874 | 4/1997 |
| WO | WO 98/12183 | 3/1998 |
| WO | WO 99/28300 | 6/1999 |
| WO | WO 01/00586 | 1/2001 |
| WO | WO 01/30762 A1 | 5/2001 |
| WO | WO 01/51472 | 7/2001 |
| WO | WO 01/81334 | 11/2001 |
| WO | WO 02/22801 A2 | 3/2002 |
| WO | WO 02/40453 A | 5/2002 |
| WO | WO 02/076950 | 10/2002 |
| WO | WO 03/092374 | 11/2003 |
| WO | WO 2004/014898 | 2/2004 |
| WO | WO 2006/119411 | 11/2006 |
| WO | WO 2007/024944 | 3/2007 |
| WO | WO 2007/024949 | 3/2007 |

OTHER PUBLICATIONS

Kihara et al (1989): STN International HCAPLUS database, (Columbus, Ohio), Accession number: 1989:423402.*

Altenbach et al., Synthesis and Structure-Activity Studies on N-[5-(1H-Imidazol-4-yl)-5,6,7,8-tetrahydro-1-naphthalenyl]methanesulfonamide, an Imidasole-Containing $\alpha_{1A}$-Adrenoceptor Agonist, J. Med. Chem. (2004), 47: 3220-3235.

Amemiya et al., Synthesis and α-Adrenergic Activities of 2-and 4-Substituted Imidazoline and Imidazoline Analogues, J. Med. Chem. (1992), 35:750-755.

Bagley et al., Synthesis and $\alpha_2$-Adrenegeric Activities of Imidazole and Imidazolidine Analogues: In Vitro and In Vivo Selectivity, Medicinal Chemistry Research (1994), 4:346-364.

Branchek et al., Trace amine receptors as targets for novel therapeutics: legend, myth and fact, Curr. Opin. Phamacol. (2003), 3:90-97.

Bunzow et al., Amphetamine, 3,4-Methylenedioxymethamphetamine, Lysergic Acid Diethylamide, and Metabolites of the catecholamine Neurotransmitters Are Agonists of a Rat Trace Amine Receptor, Molecular Pharmacology (2001), 60: 1181-1188.

Carroll et al., In Vitro and In Vivo Characterization of Alpha-1A Selective Agonists and Their Utility For Stress Incontinence, Med. Chem. Res. (2004), 13:134-148.

De Bernardis et al., Conformationally Defined Adrenergic Agents. 3. Modifications to the Carbocyclic Ring of 5,6-Dihydroxy-1-(2-imidazolinyl)tetralin: Improved Separation of $\alpha_1$ and $\alpha_2$ Adrenergic Activities, J. Med. Chem. (1986), 29:1413-1417.

De Bernardis et al., Conformationally Defined Adregernic Agents. 5. Resolution, Absolute Configuration, and Pharmacological Characterization of the Enantiomers of 2-(5,6-Dihydroxy-1,2,3,4-tetrahydro-1-naphthyl)imidazoline: A Potent Agonist at α—Adrenoceptors, J. Med. Chem. (1987), 30:1011-1017.

Faust et al., Antihypertensive Agents: Derivatives of 2-Imidazoline and 1,4,5,6-Tetrahydropyrimidine, J. Org. Chem. (1961), 26: 4044-4047.

Hirashima et al., Three-Dimensional Common-Feature Hypotheses for Octopamine Agonist 2-(Arylimino)imidazolidines, Bioorganic & Medicinal Chemistry (2002), 10:117-123.

Holt, A., Imidazoline binding sites on receptors and enzymes:Emerging targets for novel antidepressant drugs?, Journal of Psychiatry & Neuroscience (2003), 28:409-414.

Jetter et al., Synthesis of 4-Substituted Imidazoles via Palladium-Catalyzed Cross-Coupling Reactions, Synthesis (1998), 829-831.

Law et al., Benzylimidazolines as $h5$-$HT_{1B/1D}$ Serotonin Receptor Ligands: A Structure-Affinity Investigation, J. Med. Chem. (1998), 41:2243-2251.

Lee et al., 4-[(N-Imidazol-2-ylmethyl)aniline]pyranopyridine Analogs as Novel Anti-Angiogenic Agents, Bull. Korean Chem. Soc. (2005), 25: 619-628.

Lindemann et al., A renaissance in trace amines inspired by a novel GPCR family, Trends in Pharmacol. Sci. (2005), 26:274-281.

Lindemann et al., Trace amine-associated receptors form structurally and functionally distinct subfamilies of novel G protein-coupled receptors, Genomics (2005), 85: 372-385.

Matsunaga et al., $C_{17,20}$ inhibitors. Part 2: Design, synthesis and structure-activity relationships of (2-naphthylmethyl)-1H-imidazoles as novel $C_{17,20}$-lyase inhibitors, Bioorganic & Medicinal Chemistry (2004), 4314.

Matsunaga et al., Synthetic studies on (1S)-6,7-dimethoxy-2-naphthyl)-1-(1H-imidazol-4-yl)2-methylpropan-1-ol as a selective $C_{17,20}$-lyase inhibitor, Tetrahedron: Asymmetry (2004), 15: 2021-2028.

McCormack et al., Autoradiographic Localization of Tryptamine Binding Sites in the Rat and Dog Central Nervous System, J. Neurosci. (1986), 6:94-101.

McLennan, P;L., The Hypothermic Effect of Clonidine and Other Imidazolidines in Relation to their Ability to Enter the Central Nervous System in Mice, European Journal of Pharmacology (1981), 69:477-482.

Mosseau et al., A high-affinity [$^3$H]tryptamine binding site in human brain, Prog. Brain Res. (1995), 106:285-291.

Nathanson, J.A.,Phenyliminoimidazolines: Characterization of a Class of Potent Agonists of Octopamine-Sensitive Adenylate Cylcase and Their Use in Understanding the Pharmacology of Octopamine Receptors, Amer. Soc. Pharmacology (1985), 28:254-268.

Ojida et al., Sterocontrolled synthesis of (1S)-1-(1H-imidazol-4-yl)-1-(6-methoxy-2-napthyl)-2-methylpropan-1-ol as a potent $C_{17,20}$-lyase inhibitor,Tetrahedron: Asymmetry (2004), 15: 1555-1559.

Olmos et al., Imidazolines stimulate release of insulin from RIN-5AH cells independently from imidazoline $I_1$ and $I_2$ receptors, European Journal of Pharmacology (1994), 262: 41-48.

Prisinzano et al., 2-(aniline)imidazolines and 2-(benzyl)imidazoline derivatives as $h5$-$HT$-$_{1D}$ serotonin receptor ligands, Bioorganic & Medicinal Chemistry Letter (2004), 14:4697-4699.

Savola et al., Cardiovascular and Sedative α-Adrenoceptor Effects of Detomidine-like Arylalkyl Imidazoles and Associated Derivatives, Drug Res. (1988), 38:29-35.

Timmermans et al., Characterization of α-Adrenoceptor Populations. Quantitive Relationships between Cardiovascular Effects Initiated at Central and Peripheral α-Adrenoceptors, J. Med. Chem. (1981), 24:502-507.

Timmermans et al., Correlations between Central Hypotensive and Peripheral Hypertensive Effects of Structurally Dissimilar Alpha-Adrenoceptor Agonists, Life Sciences (1981), 28:653-660.

Turner et al., A Facile Route to Imidazol-4-yl Anions and Their Reaction with Carbonyl Compounds, J. Org. Chem. (1991), 56: 5739-5740.

Usdin, E. and M. Sandler, Eds., Psychopharmacology Series, vol. 1: Trace Amines and the Brain (1976), 1-281.

Wentland et al., Syntehsis and Antidepressant Properties of Novel 2-Substituted 4,5-Dihydro-1H-imidazole Derivatives, J. Med. Chem. (1987), 30:1482-1489.

Zhang et al., Medetomidine Analogs as $\alpha_2$-Adrenegeric Ligands. 3. Synthesis and Biological Evaluation of a New Series of Medetomidine Analogs and Their Potential Binding Interactions with $\alpha_2$-Adrenoceptors Involving a "Methyl Pocket", J. Med. Chem. (1997), 40: 3014-3024.

Kitbunnadaj et al., Bioorganic & Medicinal Chemistry, Elsevier Science Ltd., vol. 13, No. 23 (2005) pp. 6309-6323.

* cited by examiner

SUBSTITUTED 4-IMIDAZOLES

PRIORITY TO RELATED APPLICATION(S)

This application claims the benefit of European Patent Application No. 06124182.4, filed Nov. 16, 2006, which is hereby incorporated by reference in its entirety.

FIELD OF THE INVENTION

This invention relates to compounds which have a good affinity to the trace amine associated receptors (TAARs), especially for TAAR1.

These compounds are useful in the treatment or prevention of, inter alia, disorders of the central nervous system, for example, the treatment or prevention of depression, psychosis, Parkinson's disease, anxiety and/or attention deficit hyperactivity disorder (ADHD).

The invention relates also to processes for preparing such compounds and a pharmaceutical composition comprising such a compound.

BACKGROUND OF THE INVENTION

The classical biogenic amines (serotonin, norepinephrine, epinephrine, dopamine, histamine) play important roles as neurotransmitters in the central and peripheral nervous system. Deutch, A. Y. and Roth R. H. (1990) Neurotransmitters. In *Fundamental Neuroscience*(2nd ed.) (Zigmond, M. J., Bloom, F. E., Landis, S. C., Roberts, J. L., and Squire L. R., eds.) 193-234, Academic Press. Their synthesis and storage, as well as their degradation and reuptake after release are tightly regulated. An imbalance in the levels of biogenic amines is known to be responsible for the altered brain function under many pathological conditions. Wong, M. L. and Licinio, J. (2001) *Nat. Rev. Neurosci.* 2, 343-351; Carlsson, A. et al. (2001), *Annu. Rev. Pharmacol. Toxicol.* 41, 237-260; Tuite, P. and Riss, J. (2003), *Expert Opin. Investig. Drugs* 12, 1335-1352; Castellanos, F. X. and Tannock, R. (2002), *Nat. Rev. Neurosci.* 3, 617-628.

A second class of endogenous amine compounds, the so-called trace amines (TAs) significantly overlap with the classical biogenic amines regarding structure, metabolism and subcellular localization. The TAs include p-tyramine, β-phenylethylamine, tryptamine and octopamine, and they are present in the mammalian nervous system at generally lower levels than classical biogenic amines. Usdin, E. and Sandler, M. eds. (1984), *Trace Amines and the brain*, Dekker. Their disregulation has been linked to various psychiatric diseases like schizophrenia and depression and for other conditions like attention deficit hyperactivity disorder, migraine headache, Parkinson's disease, substance abuse and eating disorders. Lindemann, L. and Hoener, M. (2005), *Trends in Pharmacol. Sci.* 26, 274-281; Branchek, T. A. and Blackburn, T. P. (2003), *Curr. Opin. Pharmacol.* 3, 90-97; Premont, R. T. et al. (2001), *Proc. Natl. Acad. Sci. U.S.A.* 98, 9474-9475.

For a long time, TA-specific receptors had only been hypothesized based on anatomically discrete high-affinity TA binding sites in the central nervous system of humans and other mammals. Mousseau, D. D. and Butterworth, R. F. (1995), *Prog. Brain Res.* 106, 285-291; McCormack, J. K. et al. (1986), *J. Neurosci.* 6, 94-101. Accordingly, the pharmacological effects of TAs were believed to be mediated through the well known machinery of classical biogenic amines, by either triggering their release, inhibiting their reuptake or by "crossreacting" with their receptor systems. Premont, R. T. et al. (2001), *Proc. Natl. Acad. Sci. U.S.A.* 98, 9474-9475; Dyck, L. E. (1989), *Life Sci.* 44, 1149-1156; Parker, E. M. and Cubeddu, L. X. (1988), *J. Pharmacol. Exp. Ther.* 245, 199-210. This view changed significantly with the recent identification of several members of a novel family of GPCRs, the trace amine associated receptors (TAARs). Lindemann, L. and Hoener, M. (2005), *Trends in Pharmacol. Sci.* 26, 274-281; Lindemann, L. et al. (2005), *Genomics* 85, 372-385.

There are 9 TAAR genes in human (including 3 pseudogenes) and 16 genes in mouse (including 1 pseudogene). The TAAR genes do not contain introns (with one exception, TAAR2 contains 1 intron) and are located next to each other on the same chromosomal segment. The phylogenetic relationship of the receptor genes, in agreement with an in-depth GPCR pharmacophore similarity comparison and pharmacological data suggest that these receptors form three distinct subfamilies. Lindemann, L. and Hoener, M. (2005), *Trends in Pharmacol. Sci.* 26, 274-281; Lindemann, L. et al. (2005), *Genomics* 85, 372-385. TAAR1 is in the first subclass of four genes (TAAR1-4) highly conserved between human and rodents. TAs activate TAAR1 via Gαs. Disregulation of TAs was shown to contribute to the aetiology of various diseases like depression, psychosis, attention deficit hyperactivity disorder, substance abuse, Parkinson's disease, migraine headache, eating disorders, metabolic disorders and therefore TAAR1 ligands have a high potential for the treatment of these diseases.

It has been found that the compounds of formula I (described below) have a good affinity to the TAARs, especially for TAAR1.

The compounds as useful in the treatment or prevention of depression, anxiety disorders, bipolar disorder, attention deficit hyperactivity disorder (ADHD), stress-related disorders, psychotic disorders such as schizophrenia, neurological diseases such as Parkinson's disease, neurodegenerative disorders such as Alzheimer's disease, epilepsy, migraine, hypertension, substance abuse and metabolic disorders such as eating disorders, diabetes, diabetic complications, obesity, dyslipidemia, disorders of energy consumption and assimilation, disorders and malfunction of body temperature homeostasis, disorders of sleep and circadian rhythm, and/or cardiovascular disorders. Preferably, the compounds are useful in the treatment or prevention of disorders of the central nervous system, for example, the treatment or prevention of depression, psychosis, Parkinson's disease, anxiety and/or attention deficit hyperactivity disorder (ADHD).

SUMMARY OF THE INVENTION

The present invention is directed to a compound of formula I,

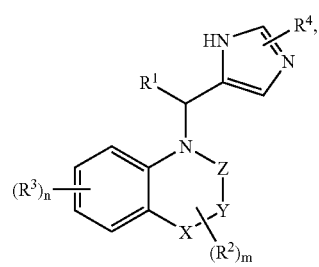

wherein
$R^1$ is selected from the group consisting of hydrogen and lower alkyl;

each $R^2$ is independently selected from the group consisting of hydrogen and lower alkyl;

each $R^3$ is independently selected from the group consisting of hydrogen, lower alkyl, lower alkoxy, phenyloxy, benzyloxy, halogen and lower alkyl substituted by halogen;

$R^4$ is selected from the group consisting of hydrogen and lower alkyl;

X is selected from the group consisting of —$CH_2$—, —CH— and —O—;

Y is selected from the group consisting of —$CH_2$—, —$CH_2CH_2$—, —CH— and a bond; with the proviso that, when X is —O—, Y is —$CH_2$—;

Z is selected from the group consisting of —$CH_2$— and —CH—;

m is 1 or 2; and n is 1 or 2;

and to a pharmaceutically-acceptable acid-addition salt of the above compound.

The present invention is also directed to processes for the preparation of the above compound.

The present invention is also directed to a pharmaceutical composition comprising the above compound or a pharmaceutically-acceptable acid-addition salt thereof.

Compounds according to the present invention have a good affinity to the TAARs, especially for TAAR1. Such compounds are useful in the treatment or prevention of illnesses such as depression, anxiety disorders, bipolar disorder, attention deficit hyperactivity disorder, stress-related disorders, psychotic disorders such as schizophrenia, neurological diseases such as Parkinson's disease, neurodegenerative disorders such as Alzheimer's disease, epilepsy, migraine, hypertension, substance abuse and metabolic disorders such as eating disorders, diabetes, diabetic complications, obesity, dyslipidemia, disorders of energy consumption and assimilation, disorders and malfunction of body temperature homeostasis, disorders of sleep and circadian rhythm, and cardiovascular disorders. Preferably, the compounds of the present invention are useful in the treatment or prevention of disorders of the central nervous system, for example, the treatment or prevention of depression, psychosis, Parkinson's disease, anxiety and/or attention deficit hyperactivity disorder (ADHD).

DETAILED DESCRIPTION OF THE INVENTION

The present invention relates to a compound of formula I,

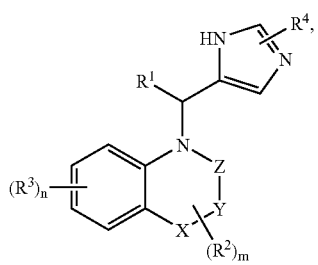

I wherein $R^1$ is selected from the group consisting of hydrogen and lower alkyl;

each $R^2$ is independently selected from the group consisting of hydrogen and lower alkyl;

each $R^3$ is independently selected from the group consisting of hydrogen, lower alkyl, lower alkoxy, phenyloxy, benzyloxy, halogen and lower alkyl substituted by halogen;

$R^4$ is selected from the group consisting of hydrogen and lower alkyl;

X is selected from the group consisting of —$CH_2$—, —CH— and —O—;

Y is selected from the group consisting of —$CH_2$—, —$CH_2CH_2$—, —CH— and a bond; with the proviso that, when X is —O—, Y is —$CH_2$—;

Z is selected from the group consisting of —$CH_2$— and —CH—;

m is 1 or 2; and n is 1 or 2;

and to a pharmaceutically-acceptable acid-addition salt of the above compound.

Such compounds have a good affinity to the trace amino associated receptors (TAARs), especially for TAAR1, and are useful in the treatment or prevention of illnesses such as depression, anxiety disorders, bipolar disorder, attention deficit hyperactivity disorder, stress-related disorders, psychotic disorders such as schizophrenia, neurological diseases such as Parkinson's disease, neurodegenerative disorders such as Alzheimer's disease, epilepsy, migraine, hypertension, substance abuse and metabolic disorders such as eating disorders, diabetes, diabetic complications, obesity, dyslipidemia, disorders of energy consumption and assimilation, disorders and malfunction of body temperature homeostasis, disorders of sleep and circadian rhythm, and cardiovascular disorders.

In preferred embodiments, the compounds of the present invention, or their pharmaceutically-acceptable acid-addition salts, are useful in the treatment or prevention of disorders of the central nervous system, for example, the treatment or prevention of depression, psychosis, Parkinson's disease, anxiety and/or attention deficit hyperactivity disorder (ADHD).

The term "benzyloxy" refers to a $C_6H_5$—$CH_2$—O— substituent.

The term "halogen" refers to chlorine, iodine, fluorine or bromine.

As used herein, the term "lower alkyl" denotes a saturated straight- or branched-chain hydrocarbon group containing from 1 to 7 carbon atoms, for example, methyl, ethyl, propyl, isopropyl, n-butyl, i-butyl, 2-butyl, t-butyl and the like. Preferred lower alkyl groups are groups with 1 to 4 carbon atoms.

As used herein, the term "lower alkyl substituted by halogen" denotes a lower alkyl group as defined above, wherein at least one hydrogen atom is replaced by halogen, for example —$CF_3$, —$CHF_2$, —$CH_2F$, —$CH_2CF_3$, —$CH_2CH_2CF_3$, —$CH_2CF_2CF_3$ and the like.

As used herein, the term "lower alkoxy" denotes a substituent in which a lower alkyl group is attached to the remainder of the molecule via an oxygen atom.

The term "pharmaceutically-acceptable acid-addition salt" embraces salts of a compound of formula I with inorganic and organic acids, such as hydrochloric acid, nitric acid, sulfuric acid, phosphoric acid, citric acid, formic acid, fumaric acid, maleic acid, acetic acid, succinic acid, tartaric acid, methanesulfonic acid, p-toluenesulfonic acid and the like, the salt not being toxic and not interfering with the ability of the compound of formula I to elicit the biological or medical response of a tissue system, animal or human, that is being sought by the researcher, veterinarian, medical doctor or other clinician.

The term "phenyloxy" refers to a $C_6H_5$—O— substituent.

In a preferred embodiment, the compound of the present invention is a compound of formula I wherein X is —$CH_2$— and Y is a bond or a pharmaceutically-acceptable acid-addition salt thereof. Examples of such compounds include:
(R,S)-(1H-imidazol-4-ylmethyl)-2-methyl-2,3-dihydro-1H-indole;
1-(3H-imidazol-4-ylmethyl)-2,3-dihydro-1H-indole;
5-bromo-1-(1H-imidazol-4-ylmethyl)-2,3-dihydro-1H-indole;
5-chloro-1-(H-imidazol-4-ylmethyl)-2,3-dihydro-1H-indole;
(R,S)-5-chloro-1-(1H-imidazol-4-ylmethyl)-2-methyl-2,3-dihydro-1H-indole;
7-ethyl-1-(H-imidazol-4-ylmethyl)-2,3-dihydro-1H-indole;
4-chloro-1-(1H-imidazol-4-ylmethyl)-2,3-dihydro-1H-indole;
1-(1H-imidazol-4-ylmethyl)-5-methoxy-2,3-dihydro-1H-indole;
1-(1H-imidazol-4-ylmethyl)-6-methoxy-2,3-dihydro-1H-indole;
1-(1H-imidazol-4-ylmethyl)-7-methoxy-2,3-dihydro-1H-indole;
1-(1H-imidazol-4-ylmethyl)-5-methyl-2,3-dihydro-1H-indole;
1-(1H-imidazol-4-ylmethyl)-4-methoxy-2,3-dihydro-1H-indole;
7-chloro-1-(1H-imidazol-4-ylmethyl)-2,3-dihydro-1H-indole;
1-(1H-imidazol-4-ylmethyl)-6-methyl-2,3-dihydro-1H-indole;
(R,S)-1-(1H-imidazol-4-ylmethyl)-3-methyl-2,3-dihydro-1H-indole;
5-fluoro-1-(H-imidazol-4-ylmethyl)-2,3-dihydro-1H-indole;
6-fluoro-1-(1H-imidazol-4-ylmethyl)-2,3-dihydro-1H-indole;
5,6-difluoro-1-(1H-imidazol-4-ylmethyl)-2,3-dihydro-1H-indole;
(R,S)-5-fluoro-1-(H-imidazol-4-ylmethyl)-2-methyl-2,3-dihydro-1H-indole;
1-(1H-imidazol-4-ylmethyl)-7-methyl-2,3-dihydro-1H-indole;
1-(1H-imidazol-4-ylmethyl)-4-methyl-2,3-dihydro-1H-indole; and pharmaceutically-acceptable acid-addition salts of such compounds.

In another preferred embodiment, the compound is a compound of formula I wherein X is —$CH_2$— and Y is —$CH_2$— or a pharmaceutically-acceptable acid-addition salt thereof. Examples of such compounds include:
R,S)-1-(1H-imidazol-4-ylmethyl)-2-methyl-1,2,3,4-tetrahydro-quinoline;
(R,S)-6-fluoro-1-(1H-imidazol-4-ylmethyl)-2-methyl-1,2,3,4-tetrahydro-quinoline;
1-(3H-imidazol-4-ylmethyl)-1,2,3,4-tetrahydro-quinoline;
6-bromo-1-(1H-imidazol-4-ylmethyl)-1,2,3,4-tetrahydro-quinoline;
(−)-1-(1H-imidazol-4-ylmethyl)-2-methyl-1,2,3,4-tetrahydro-quinoline;
5-benzyloxy-1-(1H-imidazol-4-ylmethyl)-1,2,3,4-tetrahydro-quinoline;
7-benzyloxy-1-(1H-imidazol-4-ylmethyl)-1,2,3,4-tetrahydro-quinoline;
1-(1H-imidazol-4-ylmethyl)-5-phenoxy-1,2,3,4-tetrahydro-quinoline; and pharmaceutically-acceptable acid-addition salts of such compounds.

In a further preferred embodiment, the compound is a compound of formula I wherein X is O and Y is —$CH_2$— or a pharmaceutically-acceptable acid-addition salt thereof. Examples of such compounds include:
4-(1H-imidazol-4-ylmethyl)-3,4-dihydro-2H-benzo[1,4]oxazine;
(R,S)-4-(1H-imidazol-4-ylmethyl)-3-methyl-3,4-dihydro-2H-benzo[1,4]oxazine;
(−)-4-(1H-imidazol-4-ylmethyl)-3-methyl-3,4-dihydro-2H-benzo[1,4]oxazine; and pharmaceutically-acceptable acid-addition salts of such compounds.

In yet another preferred embodiment, the compound is a compound of formula I wherein X is —$CH_2$— and Y is —$CH_2$ $CH_2$— or a pharmaceutically-acceptable acid-addition salt thereof. Examples of such compounds include:
1-(3H-imidazol-4-ylmethyl)-7-methoxy-2,3,4,5-tetrahydro-1H-benzo[b]azepine;
1-(3H-imidazol-4-ylmethyl)-2,3,4,5-tetrahydro-1H-benzo[b]azepine; and pharmaceutically-acceptable acid-addition salts of such compounds.

The present compounds of formula I and their pharmaceutically-acceptable acid-addition salts can be prepared by methods known in the art, for example, by processes described below.

One such process comprises reductively aminating a compound of formula II,

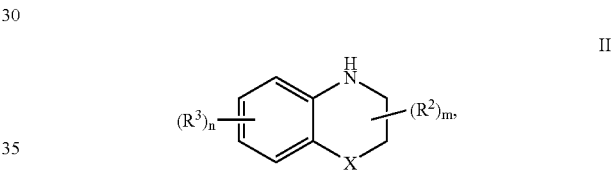

and a compound of formula III,

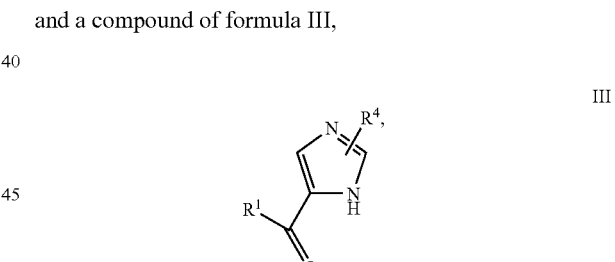

to produce a compound of formula I,

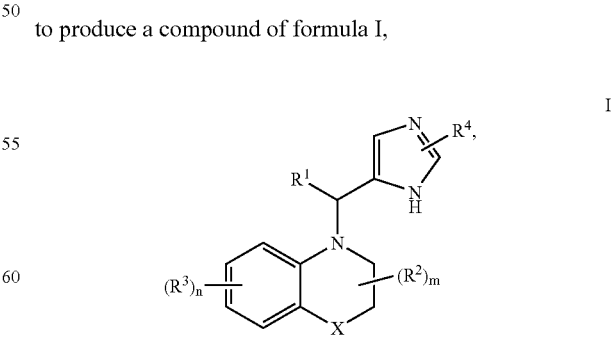

wherein, in the above formulas,
$R^1$ is selected from the group consisting of hydrogen and lower alkyl;

each $R^2$ is independently selected from the group consisting of hydrogen and lower alkyl;
each $R^3$ is independently selected from the group consisting of hydrogen, lower alkyl, lower alkoxy, phenyloxy, benzyloxy, halogen and lower alkyl substituted by halogen;
$R^4$ is selected from the group consisting of hydrogen and lower alkyl;
X is selected from the group consisting of —$CH_2$—, —CH— and —O—;
m is 1 or 2; and
n is 1 or 2.

Another such process comprises reductively aminating a compound of formula IV,

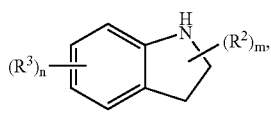

IV and a compound of formula III,

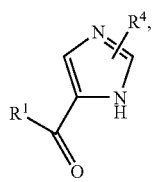

III to produce a compound of formula I-1,

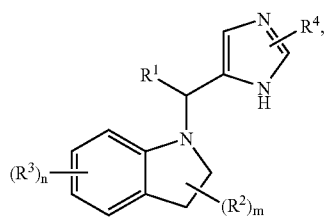

I-1 wherein, in the above formulas,
$R^1$ is selected from the group consisting of hydrogen and lower alkyl;
each $R^2$ is independently selected from the group consisting of hydrogen and lower alkyl;
each $R^3$ is independently selected from the group consisting of hydrogen, lower alkyl, lower alkoxy, phenyloxy, benzyloxy, halogen and lower alkyl substituted by halogen;
$R^4$ is selected from the group consisting of hydrogen and lower alkyl;
m is 1 or 2; and
n is 1 or 2.

Yet another such process comprises reductively aminating a compound of formula VI,

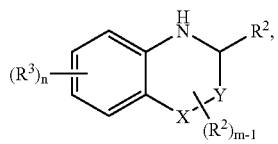

VI and a compound of formula III,

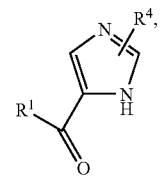

III to produce a compound of formula I-2,

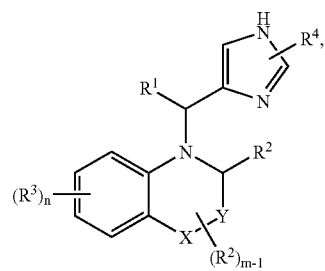

I-2 wherein, in the above formulas,
$R^1$ is selected from the group consisting of hydrogen and lower alkyl;
each $R^2$ is independently selected from the group consisting of hydrogen and lower alkyl;
each $R^3$ is independently selected from the group consisting of hydrogen, lower alkyl, lower alkoxy, phenyloxy, benzyloxy, halogen and lower alkyl substituted by halogen;
$R^4$ is selected from the group consisting of hydrogen and lower alkyl;
X is selected from the group consisting of —$CH_2$—, —CH— and —O—;
Y is selected from the group consisting of —$CH_2$—, —$CH_2CH_2$—, —CH— and a bond; with the proviso that, when X is —O—, Y is —$CH_2$—;
m is 1 or 2; and
n is 1 or 2.

Yet another such process comprises reductively aminating a compound of formula XI,

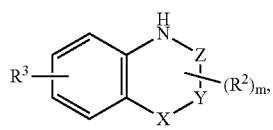

XI and a compound of formula III,

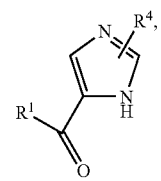

III to produce a compound of formula I-3,

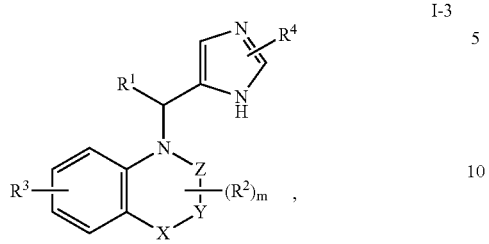

I-3 wherein, in the above formulas,
$R^1$ is selected from the group consisting of hydrogen and lower alkyl;
each $R^2$ is independently selected from the group consisting of hydrogen and lower alkyl;
each $R^3$ is independently selected from the group consisting of hydrogen, lower alkyl, lower alkoxy, phenyloxy, benzyloxy, halogen and lower alkyl substituted by halogen;
$R^4$ is selected from the group consisting of hydrogen and lower alkyl;
X is selected from the group consisting of —$CH_2$—, —CH— and —O—;
Y is selected from the group consisting of —$CH_2$—, —$CH_2CH_2$—, —CH— and a bond; with the proviso that, when X is —O—, Y is —$CH_2$—;
Z is selected from the group consisting of —$CH_2$— and —CH—.
m is 1 or 2; and
n is 1 or 2.

If desired, the compound obtained by one of the processes described above may be converted into a pharmaceutically-acceptable acid-addition salt.

The following are general schemes which exemplify the use of the above processes in the production of compounds of formula I. The starting materials are either commercially available (e.g., from one or more of the following chemical suppliers such as Aldrich, Fluka, Acros, Maybridge, Avocado, TCI, or additional suppliers as indicated in databases such as Chemical Abstracts [American Chemical Society, Columbus, Ohio] or Available Chemicals Director [Elsevier MDL, San Ramon, California]), are otherwise known in the chemical literature, or may be prepared in accordance with methods well known in the art.

Method 1

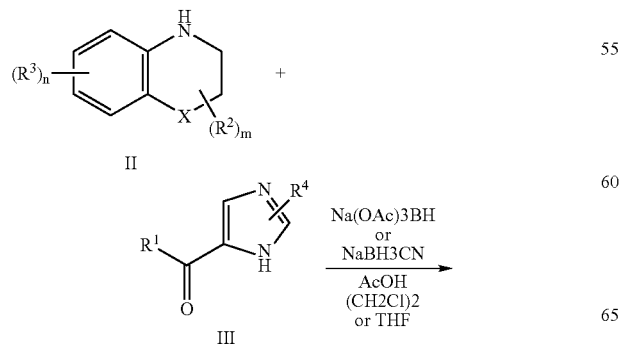

Scheme 1

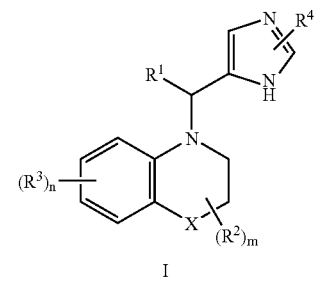

I

Scheme 1 describes the reductive amination using a 1,2,3,4-tetrahydroquinoline (X is $CH_2$) or a 3,4-dihydro-2H-benzo[1,4]oxazine (X is oxygen) of formula II as the amine component and imidazole-4-carboxaldehyde ($R^1$ is hydrogen) or (imidazole-4-yl)-alkyl-ketone ($R^1$ is alkyl) of formula III as the carbonyl component.

Method 2

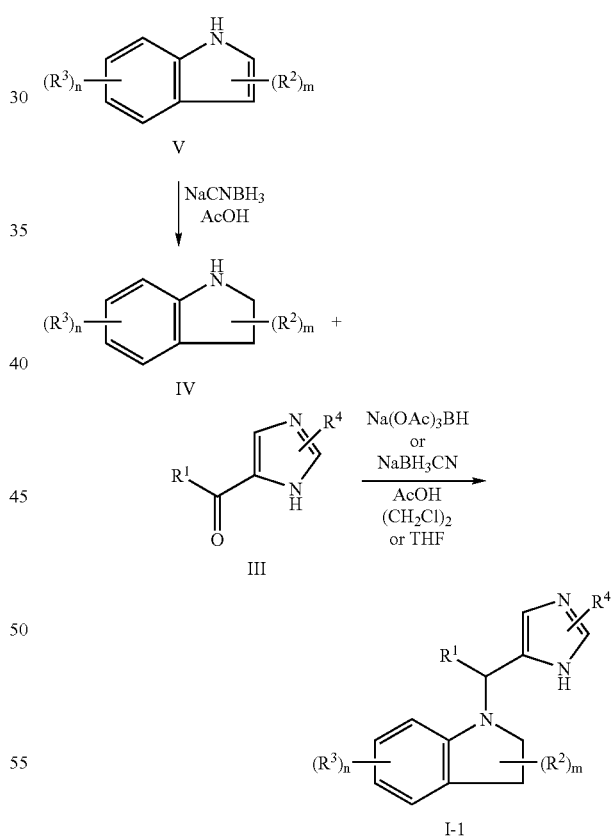

Scheme 2

I-1

Scheme 2 describes the reductive amination using an indoline compound as the amine component of formula IV and imidazole-4-carboxaldehyde ($R^1$ is hydrogen) or (imidazole-4-yl)-alkyl-ketone ($R^1$ is alkyl) of formula III as the carbonyl component. The indoline compounds may be prepared by reduction of the corresponding indole analogues of formula V.

Method 3

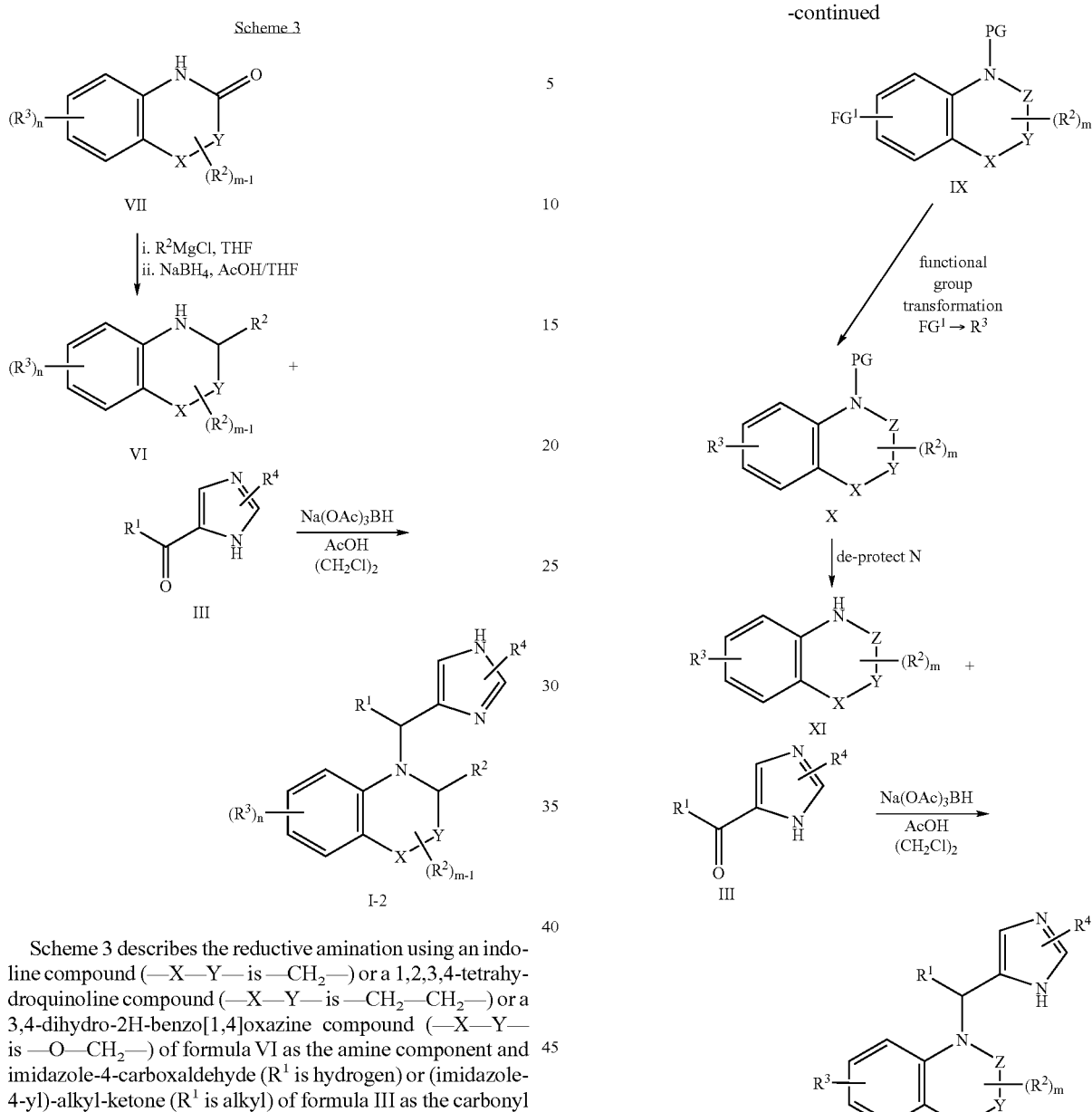

Scheme 3 describes the reductive amination using an indoline compound (—X—Y— is —CH$_2$—) or a 1,2,3,4-tetrahydroquinoline compound (—X—Y— is —CH$_2$—CH$_2$—) or a 3,4-dihydro-2H-benzo[1,4]oxazine compound (—X—Y— is —O—CH$_2$—) of formula VI as the amine component and imidazole-4-carboxaldehyde (R$^1$ is hydrogen) or (imidazole-4-yl)-alkyl-ketone (R$^1$ is alkyl) of formula III as the carbonyl component. The amino compounds can be prepared from the corresponding 1,3-dihydro-indol-2-one compound (—X—Y— is —CH$_2$—) or a 3,4-dihydro-2(1H)-quinolinone compound (—X—Y— is —CH$_2$—CH$_2$—) or a 2H-1,4-benzoxazin-3(4H)-one compound (—X—Y— is —O—CH$_2$—) of formula VII by addition of a Grignard reagent followed by reduction.

Method 4

PG = a nitrogen protecting group stable to conditions used to transform FG$^1$ into R$^3$, e.g. tert-butoxycarbonyl (BOC)

The above scheme depicts a case in which the starting material bears a reactive functional group (denoted above as FG$^1$) on the aryl ring. An example of such a functional group is a free hydroxy group. In such cases, it may be possible to perform a functional group transformation before carrying out the reductive amination step. In order to carry out the desired functional group transformation it will frequently prove advantageous to first protect the nitrogen atom which is subsequently required to participate in the reductive amination step. For instance, this nitrogen atom may be protected by conversion to a tert-butyl carbamate moiety. Examples of functional group transformations include common functional group transformations already described in the chemical literature, such as transformation of hydroxyl (as FG$^1$) to alkyl ether (as $R^3$) by treatment with a base such as sodium hydride and an alkylating agent such as an alkyl halide. Another possible functional group transformation is the transformation of hydroxyl (as $FG^1$) to aryl ether (as $R^3$) by treatment with an aryl boronic acid and copper(II) acetate according to the method of Evans et al. (*Tetrahedron Lett.* 1998, 39, 2937-2940).

Isolation and Purification of the Compounds

Isolation and purification of the compounds and intermediates described herein can be effected, if desired, by any suitable separation or purification procedure such as, for example, filtration, extraction, crystallization, column chromatography, thin-layer chromatography, thick-layer chromatography, preparative low or high-pressure liquid chromatography or a combination of these procedures. Specific illustrations of suitable separation and isolation procedures can be had by reference to the preparations and examples herein below. However, other equivalent separation or isolation procedures could, of course, also be used. Racemic mixtures of chiral compounds of formula I can be separated using chiral HPLC.

Salts of Compounds of Formula I

The compounds of formula I are basic and may be converted to a corresponding acid-addition salt. The conversion is accomplished by treatment with at least a stoichiometric amount of an appropriate acid, such as hydrochloric acid, hydrobromic acid, sulfuric acid, nitric acid, phosphoric acid and the like, and organic acids such as acetic acid, propionic acid, glycolic acid, pyruvic acid, oxalic acid, malic acid, malonic acid, succinic acid, maleic acid, fumaric acid, tartaric acid, citric acid, benzoic acid, cinnamic acid, mandelic acid, methanesulfonic acid, ethanesulfonic acid, p-toluenesulfonic acid, salicylic acid and the like. Typically, the free base is dissolved in an inert organic solvent such as diethyl ether, ethyl acetate, chloroform, ethanol or methanol and the like, and the acid added in a similar solvent. The temperature is maintained between 0° C. and 50° C. The resulting salt precipitates spontaneously or may be brought out of solution with a less polar solvent.

The acid-addition salts of the basic compounds of formula I may be converted to the corresponding free bases by treatment with at least a stoichiometric equivalent of a suitable base such as sodium or potassium hydroxide, potassium carbonate, sodium bicarbonate, ammonia, and the like.

Another aspect of the present invention is a pharmaceutical composition comprising a compound of formula I, or a pharmaceutically-acceptable acid-addition salt thereof, and a therapeutically-inert carrier. Processes for the production of such a composition are also aspects of the present invention. Such a process comprises bringing one or more compounds of formula I and/or a pharmaceutically-acceptable salt(s) thereof and, if desired, one or more other therapeutically-valuable substances into a galenical administration form together with one or more therapeutically-inert carriers.

The term "therapeutically-inert carrier" means that the carrier is not toxic and does not interfere with the ability of the active compound(s) to elicit the biological or medical response of a tissue system, animal or human that is being sought by the researcher, veterinarian, medical doctor or other clinician. The therapeutically-inert carrier for use in the composition of the present invention may be inorganic or organic. Lactose, corn starch or derivatives thereof, talc, stearic acids or its salts and the like can be used, for example, as such carriers for tablets, coated tablets, dragées and hard gelatine capsules. Suitable carriers for soft gelatine capsules are, for example, vegetable oils, waxes, fats, semi-solid and liquid polyols and the like. Depending on the nature of the active substance, no carriers are however usually required in the case of soft gelatine capsules. Suitable carriers for the production of solutions and syrups are, for example, water, polyols, glycerol, vegetable oil and the like. Suitable carriers for suppositories are, for example, natural or hardened oils, waxes, fats, semi-liquid or liquid polyols and the like.

The pharmaceutical composition can, moreover, contain preservatives, solubilizers, stabilizers, wetting agents, emulsifiers, sweeteners, colorants, flavorants, salts for varying the osmotic pressure, buffers, masking agents and antioxidants. The composition can also contain still other therapeutically valuable substances.

The pharmaceutical composition of the present invention can be administered orally, e.g. in the form of tablets, coated tablets, dragées, hard and soft gelatine capsules, solutions, emulsions or suspensions. The administration can, however, also be effected rectally, e.g. in the form of suppositories, and parenterally, e.g. in the form of injection solutions.

The present invention relates also to a method for treating or preventing a disease or disorder in a patient comprising administering a therapeutically-effective amount of a compound of the present invention to a patient. A "therapeutically-effective amount" is the amount of the subject compound that will elicit the biological or medical response of a tissue system, animal or human that is being sought by the researcher, veterinarian, medical doctor or other clinician. The above method may involve the administration of a composition which comprises a therapeutically-effective amount of the compound such as the composition described above.

The therapeutically-effective amount can vary within wide limits and will, of course, have to be adjusted to the individual requirements in each particular case. In the case of oral administration, the dosage for adults can vary from about 0.01 mg to about 1000 mg per day of a compound of general formula I or of the corresponding amount of a pharmaceutically-acceptable acid-addition salt thereof. The daily dosage may be administered as single dose or in divided doses and, in addition, the upper limit can also be exceeded when this is found to be indicated.

EXAMPLES

The following examples illustrate the invention but are not intended to limit its scope.

Example 1

(R,S)-1-(1H-Imidazol-4-ylmethyl)-2-methyl-2,3-dihydro-1H-indole

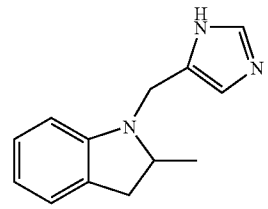

To a solution of 2-methylindoline (0.50 g, 5.20 mmol) in 1,2-dichloroethane (12 ml) were added sequentially imidazole-4-carboxaldehyde (0.75 g, 7.81 mmol), sodium triacetoxyborohydride (3.31 g, 15.6 mmol) and acetic acid (0.06 ml, 1.04 mmol). The reaction mixture was shaken at 40° C.

for 16 hours, then triethylamine (0.5 ml) was added and the mixture shaken for a further 5 minutes. The resulting suspension was filtered and the filtrate was concentrated in vacuo. The residue was purified by chromatography on silica gel (eluant: methanol/dichloromethane gradient) to yield the title compound as a white solid (0.28 g, 25%); MS (ISP): 214.1 ([M+H]$^+$).

Example 2

1-(3H-Imidazol-4-ylmethyl)-2,3-dihydro-1H-indole

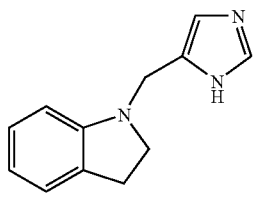

Analogously to Example 1, the title compound was obtained from indoline, imidazole-4-carboxaldehyde, sodium triacetoxyborohydride and acetic acid in 1,2-dichloroethane. MS (ISP): 200.1 ([M+H]$^+$).

Example 3

(R,S)-1-(1H-Imidazol-4-ylmethyl)-2-methyl-1,2,3,4-tetrahydro-quinoline

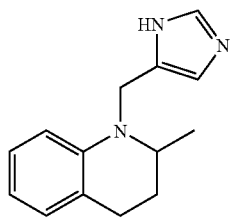

Analogously to Example 1, the title compound was obtained from 1,2,3,4-tetrahydroquinaldine, imidazole-4-carboxaldehyde, sodium triacetoxyborohydride and acetic acid in 1,2-dichloroethane. MS (ISP): 228.4 ([M+H]$^+$).

Example 4

5-Bromo-1-(1H-imidazol-4-ylmethyl)-2,3-dihydro-1H-indole

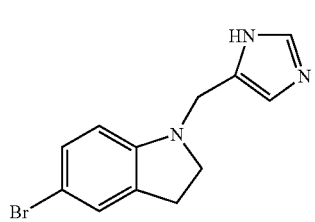

Analogously to Example 1, the title compound was obtained from 5-bromoindoline, imidazole-4-carboxaldehyde, sodium triacetoxyborohydride and acetic acid in 1,2-dichloroethane. MS (ISP): 280.1 ([{$^{81}$Br}M+H]$^+$), 278.1 ([{$^{79}$Br}M+H]$^+$).

Example 5

1-(1H-Imidazol-4-ylmethyl)-6-trifluoromethyl-2,3-dihydro-1H-indole

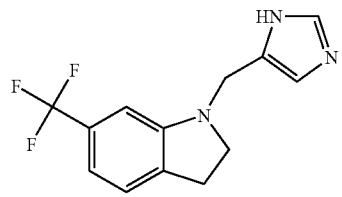

Analogously to Example 1, the title compound was obtained from 6-(trifluoromethyl)indoline, imidazole-4-carboxaldehyde, sodium triacetoxyborohydride and acetic acid in 1,2-dichloroethane. MS (ISP): 268.3 ([M+H]$^+$).

Example 6

(R,S)-6-Fluoro-1-(1H-imidazol-4-ylmethyl)-2-methyl-1,2,3,4-tetrahydro-quinoline

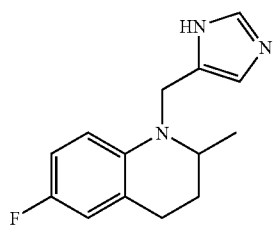

Analogously to Example 1, the title compound was obtained from 6-fluoro-2-methyl-1,2,3,4-tetrahydroquinoline, imidazole-4-carboxaldehyde, sodium triacetoxyborohydride and acetic acid in 1,2-dichloroethane. MS (ISP): 246.3 ([M+H]$^+$).

Example 7

1-(3H-Imidazol-4-ylmethyl)-1,2,3,4-tetrahydro-quinoline

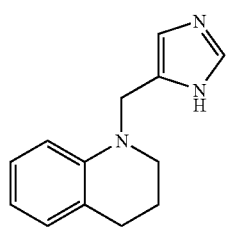

Analogously to Example 1, the title compound was obtained from 1,2,3,4-tetrahydroquinoline, imidazole-4-carboxaldehyde, sodium triacetoxyborohydride and acetic acid in 1,2-dichloroethane. MS (ISP): 214.4 ([M+H]$^+$).

Example 8

(R,S)-2-Methyl-1-(2-methyl-1H-imidazol-4-ylmethyl)-2,3-dihydro-1H-indole

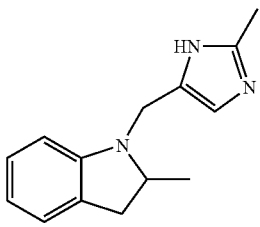

Analogously to Example 1, the title compound was obtained from 2-methylindoline, 2-methyl-imidazole-4-carboxaldehyde, sodium triacetoxyborohydride and acetic acid in 1,2-dichloroethane. MS (ISP): 228.4 ([M+H]$^+$).

Example 9

2-Methyl-1-(2-methyl-1H-imidazol-4-ylmethyl)-1,2,3,4-tetrahydro-quinoline

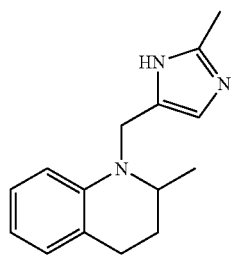

Analogously to Example 1, the title compound was obtained from 1,2,3,4-tetrahydroquinaldine, 2-methyl-imidazole-4-carboxaldehyde, sodium triacetoxyborohydride and acetic acid in 1,2-dichloroethane. MS (ISP): 242.3 ([M+H]$^+$).

Example 10

5-Bromo-1-(2-methyl-1H-imidazol-4-ylmethyl)-2,3-dihydro-1H-indole

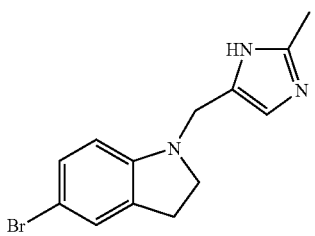

Analogously to Example 1, the title compound was obtained from 5-bromoindoline, 2-methyl-imidazole-4-carboxaldehyde, sodium triacetoxyborohydride and acetic acid in 1,2-dichloroethane. MS (ISP): 294.0 ([{$^{81}$Br}M+H]$^+$), 292.0 ([{$^{79}$Br}M+H]$^+$).

Example 11

1-(2-Methyl-1H-imidazol-4-ylmethyl)-6-trifluoromethyl-2,3-dihydro-1H-indole

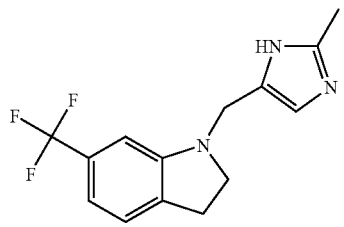

Analogously to Example 1, the title compound was obtained from 6-(trifluoromethyl)indoline, 2-methyl-imidazole-4-carboxaldehyde, sodium triacetoxyborohydride and acetic acid in 1,2-dichloroethane. MS (ISP): 282.3 ([M+H]$^+$).

Example 12

(R,S)-6-Fluoro-2-methyl-1-(2-methyl-1H-imidazol-4-ylmethyl)-1,2,3,4-tetrahydro-quinoline

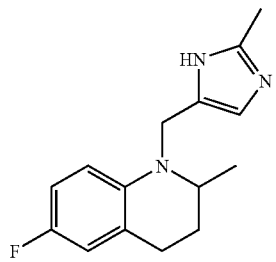

Analogously to Example 1, the title compound was obtained from 6-fluoro-2-methyl-1,2,3,4-tetrahydroquinoline, 2-methyl-imidazole-4-carboxaldehyde, sodium triacetoxyborohydride and acetic acid in 1,2-dichloroethane. MS (ISP): 260.3 ([M+H]$^+$).

Example 13

1-(2-Methyl-1H-imidazol-4-ylmethyl)-1,2,3,4-tetrahydro-quinoline

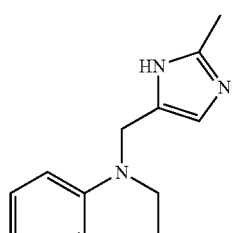

Analogously to Example 1, the title compound was obtained from 1,2,3,4-tetrahydroquinoline, 2-methyl-imidazole-4-carboxaldehyde, sodium triacetoxyborohydride and acetic acid in 1,2-dichloroethane. MS (ISP): 228.6 ([M+H]$^+$).

Example 14

5-Chloro-1-(1H-imidazol-4-ylmethyl)-2,3-dihydro-1H-indole

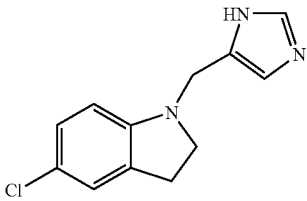

Analogously to Example 1, the title compound was obtained from 5-chloroindoline, imidazole-4-carboxaldehyde, sodium triacetoxyborohydride and acetic acid in 1,2-dichloroethane. MS (ISP): 236.2 ([{$^{37}$Cl}M+H]$^+$), 234.2 ([{$^{35}$Cl}M+H]$^+$).

Example 15

5-Chloro-1-(2-methyl-1H-imidazol-4-ylmethyl)-2,3-dihydro-1H-indole

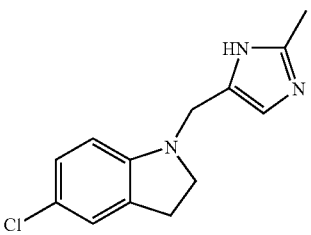

Analogously to Example 1, the title compound was obtained from 5-chloroindoline, 2-methyl-imidazole-4-carboxaldehyde, sodium triacetoxyborohydride and acetic acid in 1,2-dichloroethane. MS (ISP): 250.1 ([{$^{37}$Cl}M+H]$^+$), 248.2 ([{$^{35}$Cl}M+H]$^+$).

Example 16

(R,S)-5-Chloro-1-(1H-imidazol-4-ylmethyl)-2-methyl-2,3-dihydro-1H-indole

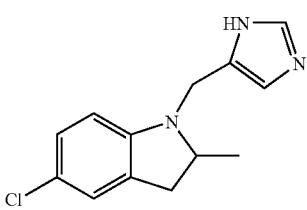

(a) (R,S)-5-Chloro-2-methyl-2,3-dihydro-1H-indole

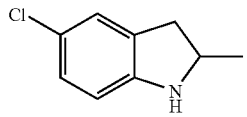

To a solution of 5-chloro-2-methylindole (1.00 g, 6.04 mmol) in acetic acid (7 ml) was added portion-wise sodium cyanoborohydride (0.76 g, 12.1 mmol) and the reaction mixture was stirred at room temperature for 16 hours. The resulting solution was diluted with ethyl acetate and washed sequentially with water and with 5 N aq. sodium hydroxide solution. The organic phase was dried over sodium sulphate and concentrated in vacuo. The residue was purified by chromatography on silica gel (eluant: heptane/ethyl acetate gradient) to yield the title compound as a colorless oil (1.00 g, 100%); MS (ISP): 170.2 ([{$^{37}$Cl}M+H]$^+$), 168.3 ([{$^{35}$Cl}M+H]$^+$).

(b) (R,S)-5-Chloro-1-(H-imidazol-4-ylmethyl)-2-meth-2,3-dihydro-1H-indole

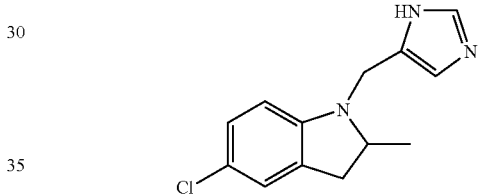

The title compound was prepared analogously to Example 1, from (R,S)-5-chloro-2-methyl-2,3-dihydro-1H-indole, imidazole-4-carboxaldehyde, sodium triacetoxyborohydride and acetic acid in 1,2-dichloroethane. MS (ISP): 250.2 ([{$^{37}$Cl}M+H]$^+$), 248.3 ([{$^{35}$C}M+H]$^+$).

Example 17

(R,S)-5-Chloro-2-methyl-1-(2-methyl-1H-imidazol-4-ylmethyl)-2,3-dihydro-1H-indole

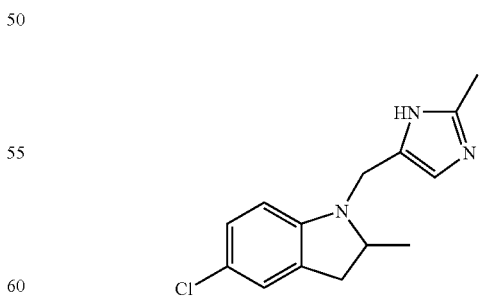

Analogously to Example 16(b), the title compound was obtained from (R,S)-5-chloro-2-methyl-2,3-dihydro-1H-indole, 2-methyl-imidazole-4-carboxaldehyde, sodium triacetoxyborohydride and acetic acid in 1,2-dichloroethane. MS (ISP): 264.2 ([{$^{37}$Cl}M+H]$^+$), 262.2 ([{$^{35}$Cl}M+H]$^+$).

Example 18

4-(1H-Imidazol-4-ylmethyl)-3,4-dihydro-2H-benzo[1,4]oxazine

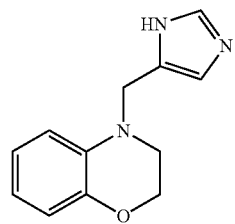

Analogously to Example 1, the title compound was obtained from 3,4-dihydro-2H-benzo[ ]1,4]oxazine, imidazole-4-carboxaldehyde, sodium triacetoxyborohydride and acetic acid in 1,2-dichloroethane. MS (ISP): 216.4 ([M+H]$^+$).

Example 19

4-(2-Methyl-1H-imidazol-4-ylmethyl)-3,4-dihydro-2H-benzo[1,4]oxazine

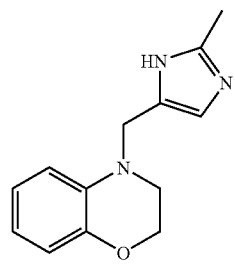

Analogously to Example 1, the title compound was obtained from 3,4-dihydro-2H-benzo[ ]1,4]oxazine, 2-methyl-imidazole-4-carboxaldehyde, sodium triacetoxyborohydride and acetic acid in 1,2-dichloroethane. MS (ISP): 230.4 ([M+H]$^+$).

Example 20

1-(2-Butyl-3H-imidazol-4-ylmethyl)-1,2,3,4-tetrahydro-quinoline

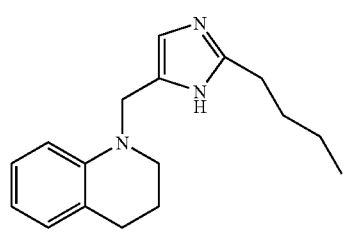

Analogously to Example 1, the title compound was obtained from 1,2,3,4-tetrahydroquinoline, 2-n-butyl-imidazole-4-carboxaldehyde, sodium cyanoborohydride and acetic acid in THF. MS (ISP): 270.4 ([M+H]$^+$).

Example 21

1-(2-Butyl-3H-imidazol-4-ylmethyl)-2,3-dihydro-1H-indole

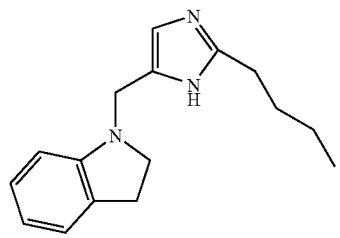

Analogously to Example 1, the title compound was obtained from indoline, 2-n-butyl-imidazole-4-carboxaldehyde, sodium cyanoborohydride and acetic acid in THF. MS (ISP): 256.4 ([M+H]$^+$).

Example 22

(2R,S,3R,S)-1-(1H-Imidazol-4-ylmethyl)-2,3-dimethyl-2,3-dihydro-H-indole

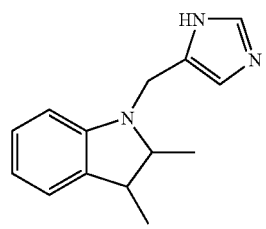

Analogously to Example 16, the title compound was obtained by reacting 2,3-dimethylindole and sodium cyanoborohydride in acetic acid, then treating the intermediate product with imidazole-4-carboxaldehyde, sodium triacetoxyborohydride and acetic acid in 1,2-dichloroethane. MS (ISP): 228.6 ([M+H]$^+$).

Example 23

7-Ethyl-1-(1H-imidazol-4-ylmethyl)-2,3-dihydro-1H-indole

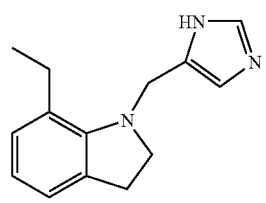

Analogously to Example 16, the title compound was obtained by reacting 7-ethylindole and sodium cyanoborohydride in acetic acid, then treating the intermediate product with imidazole-4-carboxaldehyde, sodium triacetoxyborohydride and acetic acid in 1,2-dichloroethane. MS (ISP): 228.6 ([M+H]$^+$).

Example 24

6-Chloro-1-(1H-imidazol-4-ylmethyl)-2,3-dihydro-1H-indole

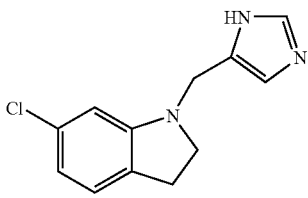

Analogously to Example 16, the title compound was obtained by reacting 6-chloroindole and sodium cyanoborohydride in acetic acid, then treating the intermediate product with imidazole-4-carboxaldehyde, sodium triacetoxyborohydride and acetic acid in 1,2-dichloroethane. MS (ISP): 236.2 ($[\{^{37}Cl\}M+H]^+$), 234.1 ($[\{^{35}Cl\}M+H]^+$).

Example 25

4-Chloro-1-(1H-imidazol-4-ylmethyl)-2,3-dihydro-1H-indole

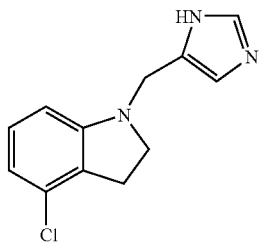

Analogously to Example 16, the title compound was obtained by reacting 4-chloroindole and sodium cyanoborohydride in acetic acid, then treating the intermediate product with imidazole-4-carboxaldehyde, sodium triacetoxyborohydride and acetic acid in 1,2-dichloroethane. MS (ISP): 236.2 ($[\{^{37}Cl\}M+H]^+$), 234.1 ($[\{^{35}Cl\}M+H]^+$).

Example 26

1-(1H-Imidazol-4-ylmethyl)-5-methoxy-2,3-dihydro-1H-indole

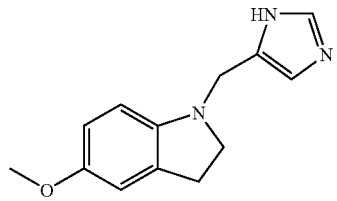

Analogously to Example 16, the title compound was obtained by reacting 5-methoxyindole and sodium cyanoborohydride in acetic acid, then treating the intermediate product with imidazole-4-carboxaldehyde, sodium triacetoxyborohydride and acetic acid in 1,2-dichloroethane. MS (ISP): 230.4 ($[M+H]^+$).

Example 27

1-(1H-Imidazol-4-ylmethyl)-6-methoxy-2,3-dihydro-1H-indole

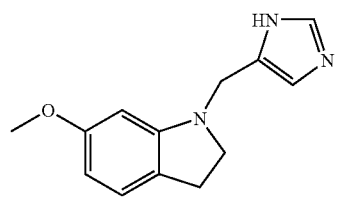

Analogously to Example 16, the title compound was obtained by reacting 6-methoxyindole and sodium cyanoborohydride in acetic acid, then treating the intermediate product with imidazole-4-carboxaldehyde, sodium triacetoxyborohydride and acetic acid in 1,2-dichloroethane. MS (ISP): 230.4 ($[M+H]^+$).

Example 28

1-(1H-Imidazol-4-ylmethyl)-7-methoxy-2,3-dihydro-1H-indole

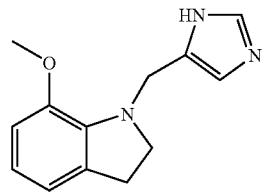

Analogously to Example 16, the title compound was obtained by reacting 7-methoxyindole and sodium cyanoborohydride in acetic acid, then treating the intermediate product with imidazole-4-carboxaldehyde, sodium triacetoxyborohydride and acetic acid in 1,2-dichloroethane. MS (ISP): 230.4 ($[M+H]^+$).

Example 29

1-(1H-Imidazol-4-ylmethyl)-5-methyl-2,3-dihydro-1H-indole

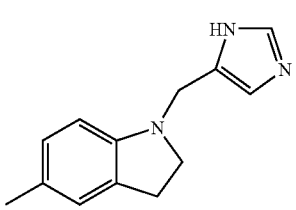

Analogously to Example 16, the title compound was obtained by reacting 5-methylindole and sodium cyanoborohydride in acetic acid, then treating the intermediate product with imidazole-4-carboxaldehyde, sodium triacetoxyborohydride and acetic acid in 1,2-dichloroethane. MS (ISP): 214.3 ([M+H]$^+$).

Example 30

(R,S)-1-(1H-Imidazol-4-ylmethyl)-5-methoxy-2-methyl-2,3-dihydro-1H-indole

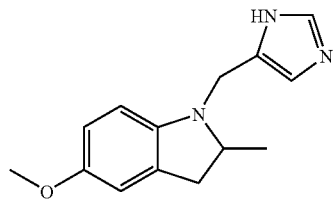

Analogously to Example 16, the title compound was obtained by reacting 5-methoxy-2-methylindole and sodium cyanoborohydride in acetic acid, then treating the intermediate product with imidazole-4-carboxaldehyde, sodium triacetoxyborohydride and acetic acid in 1,2-dichloroethane. MS (ISP): 244.4 ([M+H]$^+$).

Example 31

1-(1H-Imidazol-4-ylmethyl)-4-methoxy-2,3-dihydro-1H-indole

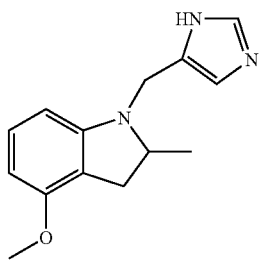

Analogously to Example 16, the title compound was obtained by reacting 4-methoxyindole and sodium cyanoborohydride in acetic acid, then treating the intermediate product with imidazole-4-carboxaldehyde, sodium triacetoxyborohydride and acetic acid in 1,2-dichloroethane. MS (ISP): 230.4 ([M+H]$^+$).

Example 32

7-Chloro-1-(H-imidazol-4-ylmethyl)-2,3-dihydro-1H-indole

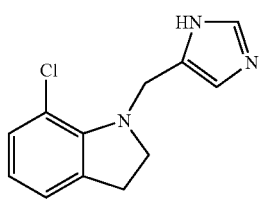

Analogously to Example 16, the title compound was obtained by reacting 7-chloroindole and sodium cyanoborohydride in acetic acid, then treating the intermediate product with imidazole-4-carboxaldehyde, sodium triacetoxyborohydride and acetic acid in 1,2-dichloroethane. MS (ISP): 236.2 ([$\{^{37}Cl\}$M+H]$^+$), 234.1 ([$\{^{35}Cl\}$M+H]$^+$).

Example 33

6-Bromo-1-(H-imidazol-4-ylmethyl)-1,2,3,4-tetrahydro-quinoline

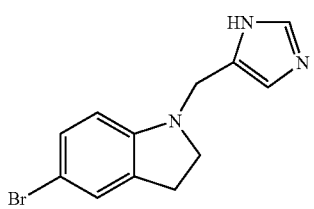

Analogously to Example 1, the title compound was obtained from 6-bromo-1,2,3,4-tetrahydro-quinoline, imidazole-4-carboxaldehyde, sodium triacetoxyborohydride and acetic acid in 1,2-dichloroethane. MS (ISP): 294.1 ([$\{^{81}Br\}$M+H]$^+$), 292.1 ([$\{^{79}Br\}$M+H]$^+$).

Example 34

1-(1H-Imidazol-4-ylmethyl)-6-methyl-2,3-dihydro-1H-indole

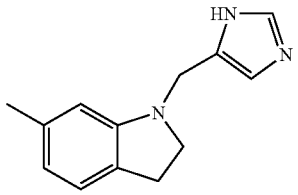

Analogously to Example 16, the title compound was obtained by reacting 6-methylindole and sodium cyanoborohydride in acetic acid, then treating the intermediate product with imidazole-4-carboxaldehyde, sodium triacetoxyborohydride and acetic acid in 1,2-dichloroethane. MS (ISP): 214.1 ([M+H]$^+$).

Example 35

(R,S)-1-(1H-Imidazol-4-ylmethyl)-3-methyl-2,3-dihydro-1H-indole

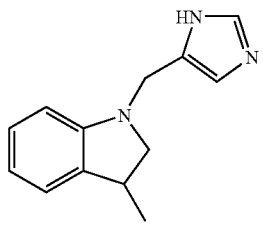

Analogously to Example 16, the title compound was obtained by reacting 3-methylindole and sodium cyanoborohydride in acetic acid, then treating the intermediate product with imidazole-4-carboxaldehyde, sodium triacetoxyborohydride and acetic acid in 1,2-dichloroethane. MS (ISP): 214.1 ([M+H]⁺).

Example 36

5-Fluoro-1-(1H-imidazol-4-ylmethyl)-2,3-dihydro-1H-indole

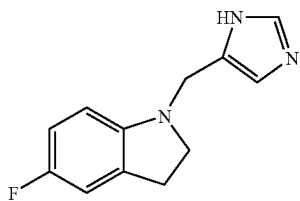

Analogously to Example 16, the title compound was obtained by reacting 5-fluoroindole and sodium cyanoborohydride in acetic acid, then treating the intermediate product with imidazole-4-carboxaldehyde, sodium triacetoxyborohydride and acetic acid in 1,2-dichloroethane. MS (ISP): 218.3 ([M+H]⁺).

Example 37

6-Fluoro-1-(1H-imidazol-4-ylmethyl)-2,3-dihydro-1H-indole

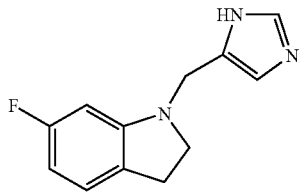

Analogously to Example 16, the title compound was obtained by reacting 6-fluoroindole and sodium cyanoborohydride in acetic acid, then treating the intermediate product with imidazole-4-carboxaldehyde, sodium triacetoxyborohydride and acetic acid in 1,2-dichloroethane. MS (ISP): 218.3 ([M+H]⁺).

Example 38

5,6-Difluoro-1-(1H-imidazol-4-ylmethyl)-2,3-dihydro-1H-indole

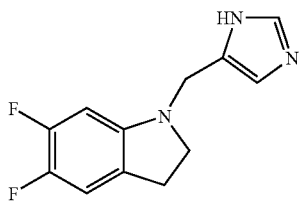

Analogously to Example 16, the title compound was obtained by reacting 5,6-difluoroindole and sodium cyanoborohydride in acetic acid, then treating the intermediate product with imidazole-4-carboxaldehyde, sodium triacetoxyborohydride and acetic acid in 1,2-dichloroethane. MS (ISP): 236.4 ([M+H]⁺).

Example 39

(R,S)-5-Fluoro-1-(1H-imidazol-4-ylmethyl)-2-methyl-2,3-dihydro-1H-indole

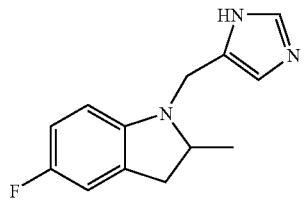

Analogously to Example 16, the title compound was obtained by reacting 5-fluoro-2-methyl-indole and sodium cyanoborohydride in acetic acid, then treating the intermediate product with imidazole-4-carboxaldehyde, sodium triacetoxyborohydride and acetic acid in 1,2-dichloroethane. MS (ISP): 232.1 ([M+H]⁺).

Example 40

1-(1H-Imidazol-4-ylmethyl)-7-methyl-2,3-dihydro-1H-indole

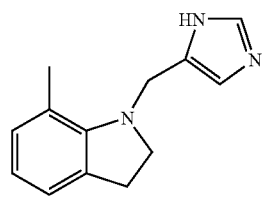

Analogously to Example 16, the title compound was obtained by reacting 7-methyl-indole and sodium cyanoborohydride in acetic acid, then treating the intermediate product with imidazole-4-carboxaldehyde, sodium triacetoxyborohydride and acetic acid in 1,2-dichloroethane. MS (ISP): 214.1 ([M+H]⁺).

Example 41

1-(1H-Imidazol-4-ylmethyl)-4-methyl-2,3-dihydro-1H-indole

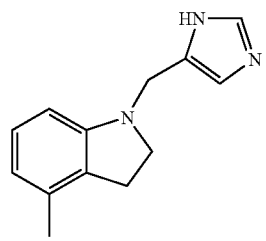

Analogously to Example 16, the title compound was obtained by reacting 4-methyl-indole and sodium cyanoborohydride in acetic acid, then treating the intermediate product with imidazole-4-carboxaldehyde, sodium triacetoxyborohydride and acetic acid in 1,2-dichloroethane. MS (ISP): 214.1 ([M+H]⁺).

Example 42

1-(5-Fluoro-1H-imidazol-4-ylmethyl)-1,2,3,4-tetrahydro-quinoline

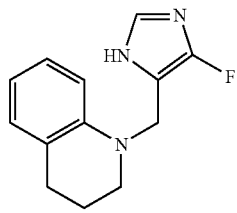

(a) 5-Fluoro-1-(2-trimethylsilanyl-ethoxymethyl)-1H-imidazole-4-carboxylic acid ethyl ester

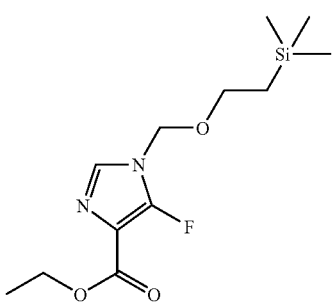

To a stirred suspension of NaH (276 mg; 55% dispersion in mineral oil) at 0° C. in dimethylformamide (DMF) (15 ml) under an argon atmosphere was added portion-wise 5-fluoro-3H-imidazole-4-carboxylic acid ethyl ester (1.0 g) over a period of 10 minutes. The ice bath was removed and the mixture (almost clear light brown solution) was stirred at room temperature for 1 hour and 30 minutes. The mixture was cooled again in an ice bath and 2-(trimethylsilyl)-ethoxymethylchloride (1.24 ml) was added over a period of 5 minutes. The mixture (slowly warming up to room temperature) was then stirred for 16 hours. The off-white slurry was diluted with ethyl acetate and washed with H$_2$O. The aqueous phase was back extracted with ethyl acetate (25 ml). The combined organics were washed with H$_2$O and brine, dried over MgSO$_4$, filtered and concentrated. The crude product was purified by column chromatography (silica gel; gradient: cyclohexane→cyclohexane/ethyl acetate 3:2) to give 5-fluoro-1-(2-trimethylsilanyl-ethoxymethyl)-1H-imidazole-4-carboxylic acid ethyl ester (1.57 g) as light yellow oil. MS (ISP): 288.9 ([M+H]$^+$).

(b) [5-Fluoro-1-(2-trimethylsilanyl-ethoxymethyl)-1H-imidazol-4-yl]-methanol

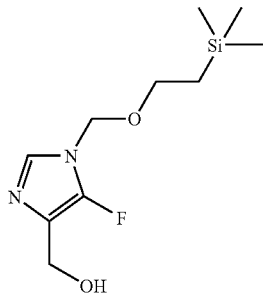

To a stirred solution of 5-fluoro-1-(2-trimethylsilanyl-ethoxymethyl)-1H-imidazole-4-carboxylic acid ethyl ester (400 mg) in toluene (10 ml) at −78° C. under an argon atmosphere was added dropwise diisobutylaluminium hydride (DIBAL) (1.72 ml; 20 wt % solution in toluene) for 10 minutes (temperature below −75° C.). After 2 hours of stirring at −78° C., conversion of the ester was found to be incomplete. More DIBAL solution (1.17 ml.) was added over a period of 5 minutes and stirring at −78° C. was continued for 1 hour and 30 minutes. The mixture was quenched by the addition of 10 ml potassium-sodium tartrate concentrated aqueous solution. The aqueous phase was back extracted with ethyl acetate. The combined organics were washed with H$_2$O and brine, dried over MgSO$_4$, filtered and concentrated to leave [5-fluoro-1-(2-trimethylsilanyl-ethoxymethyl)-1H-imidazol-4-yl]-methanol as (346 mg) as off-white solid. The crude product was used in the next reaction step without further purification. MS (ISP): 247.3 ([M+H]$^+$).

(c) 5-Fluoro-1-(2-trimethylsilanyl-ethoxymethyl)-1H-imidazole-4-carbaldehyde

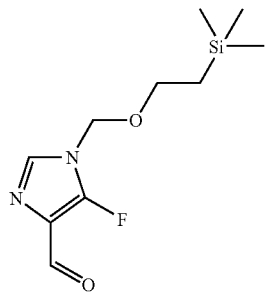

To a stirred solution of [5-fluoro-1-(2-trimethylsilanyl-ethoxymethyl)-1H-imidazol-4-yl]-methanol (339 mg) at room temperature in dichloromethane (15 ml) under an argon atmosphere was added MnO$_2$ (1.20 g). The black suspension was heated to reflux and stirring at that temperature was continued for 18 hours, then was cooled to room temperature and filtered. The resulting cake was washed with dichloromethane. The filtrate was concentrated to leave 5-fluoro-1-(2-trimethylsilanyl-ethoxymethyl)-1H-imidazole-4-carbaldehyde (262 mg) as light yellow viscous oil. The crude product was used in the next reaction step without further purification. MS (EI): 171.1 ([M-Si(Me)$_3$]).

(d) 1-[5-Fluoro-1-(2-trimethylsilanyl-ethoxymethyl)-1H-imidazol-4-ylmethyl]-1,2,3,4-tetrahydro-quinoline

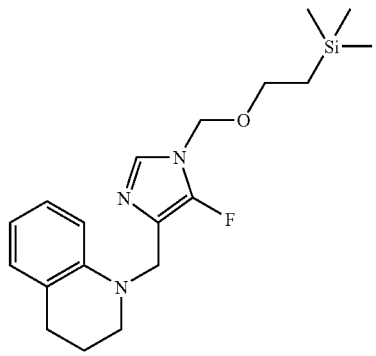

To a stirred solution of 5-fluoro-1-(2-trimethylsilanyl-ethoxymethyl)-1H-imidazole-4-carbaldehyde (202 mg) at room temperature in methanol (10 ml) under an argon atmosphere were added zinc chloride (409 mg) and 1,2,3,4-tetrahydroquinoline (100 mg). The clear light yellow solution was stirred for 4 hours and 30 minutes. Then, NaBH$_3$CN (141 mg) was added in one portion. The mixture was heated to 60° C. and stirring at that temperature was continued for 22 hours. The reaction was directly adsorbed on silica gel. The crude product was isolated by column chromatography (silica gel; gradient: cyclohexane→cyclohexane/ethyl acetate 65:35) to give 1-[5-fluoro-1-(2-trimethylsilanyl-ethoxymethyl)-1H-imidazol-4-ylmethyl]-1,2,3,4-tetrahydroquinoline (238 mg) as colorless viscous oil. MS (ISP): 362.3 ([M+H]⁺).

(e) 1-(5-Fluoro-1H-imidazol-4-ylmethyl)-1,2,3,4-tetrahydroquinoline

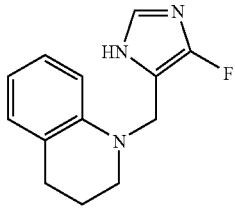

To a stirred solution of 1-[5-fluoro-1-(2-trimethylsilanyl-ethoxymethyl)-1H-imidazol-4-ylmethyl]-1,2,3,4-tetrahydroquinoline (103 mg) at room temperature in tetrahydrofuran (THF) (5 ml) under an argon atmosphere was added tetra-n-butylammonium fluoride (TBAF) (1.1 ml; 1 M solution in THF). The mixture was heated to 60° C. and stirring at that temperature was continued for 20 minutes, then the mixture was adsorbed directly on silica gel. The crude product was isolated by column chromatography (silica gel; gradient: cyclohexane→ethyl acetate) to give 1-(5-fluoro-1H-imidazol-4-ylmethyl)-1,2,3,4-tetrahydro-quinoline (32 mg) as light yellow solid. (MS (ISP): 232.1 ([M+H]⁺).

Example 43

1-(3H-Imidazol-4-ylmethyl)-7-methoxy-2,3,4,5-tetrahydro-1H-benzo[b]azepine

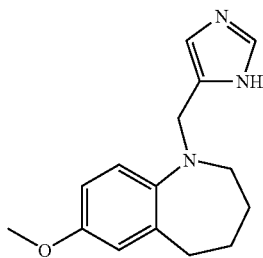

Analogously to Example 1, the title compound was obtained from 7-methoxy-2,3,4,5-tetrahydro-1H-benzo[b]azepine hydrochloride (CAS: 23561-82-2), imidazole-4-carboxaldehyde, sodium triacetoxyborohydride and acetic acid in 1,2-dichloroethane. MS (ISP): 258.3 ([M+H]⁺).

Example 44

1-(3H-Imidazol-4-ylmethyl)-2,3,4,5-tetrahydro-1H-benzo[b]azepine

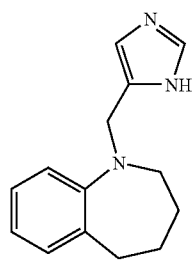

Analogously to Example 1, the title compound was obtained from 2,3,4,5-tetrahydro-1H-benzo[b]azepine, imidazole-4-carboxaldehyde, sodium triacetoxyborohydride and acetic acid in 1,2-dichloroethane. MS (ISP): 228.1 ([M+H]⁺).

Example 45

(R,S)-4-(1H-Imidazol-4-ylmethyl)-3-methyl-3,4-dihydro-2H-benzo[1,4]oxazine

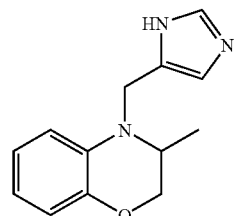

(a) (R,S)-3-Methyl-3,4-dihydro-2H-benzo[1,4]oxazine

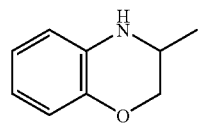

To a solution of 2H-1,4-benzoxazin-3(4H)-one (2.00 g, 13.4 mmol) in tetrahydrofuran (THF) (20 ml) was added dropwise at 5° C. a THF solution of methylmagnesium chloride (17.9 ml, 3 M, 53.7 mmol) and the reaction mixture was then stirred at 50° C. for 90 minutes. The reaction mixture was then cooled to 5° C. and quenched by dropwise addition of 20 ml acetic acid. Sodium borohydride (1.27 g, 33.5 mmol) was then added portion-wise and the mixture was stirred at room temperature overnight. The resulting suspension was then cooled to 0° C. and 3 N aq. sodium hydroxide solution was added dropwise until the mixture was pH 10. Ethyl acetate was then added, the phases separated, and the organic phase dried over sodium sulphate and concentrated in vacuo. The residue was purified by chromatography on silica gel (eluant: heptane/ethyl acetate gradient) to yield the title compound as a colorless oil (0.92 g, 46%); MS (ISP): 150.3 ([M+H]⁺).

(b) (R,S)-4-(1H-Imidazol-4-ylmethyl)-3-methyl-3,4-dihydro-2H-benzo[1,4]oxazine

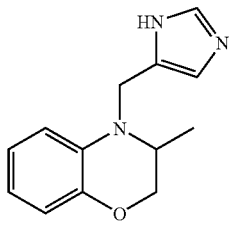

The title compound was prepared analogously to Example 1, from (R,S)-3-methyl-3,4-dihydro-2H-benzo[1,4]oxazine, imidazole-4-carboxaldehyde, sodium triacetoxyborohydride and acetic acid in 1,2-dichloroethane. MS (ISP): 230.4 ([M+H]⁺).

Example 46

(+)-1-(1H-Imidazol-4-ylmethyl)-2-methyl-1,2,3,4-tetrahydro-quinoline

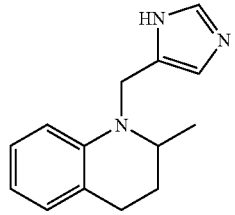

The enantiomers of (R,S)-1-(1H-imidazol-4-ylmethyl)-2-methyl-1,2,3,4-tetrahydro-quinoline (Example 3) were separated with chiral HPLC (Chiracel OD column; eluant isopropanol/heptane 10:90; flow-rate 35 ml min$^{-1}$; pressure 15 bar; retention time 65 min). MS (ISP): 228.4 ([M+H]$^+$). $[\alpha]_D^{20}$=+6.54° (c=0.52, methanol).

Example 47

(−)-1-(1H-Imidazol-4-ylmethyl)-2-methyl-1,2,3,4-tetrahydro-quinoline

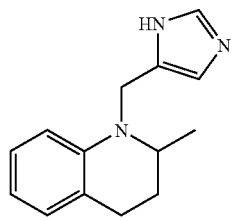

The enantiomers of (R,S)-1-(1H-imidazol-4-ylmethyl)-2-methyl-1,2,3,4-tetrahydro-quinoline (Example 3) were separated with chiral HPLC (Chiracel OD column; eluant isopropanol/heptane 10:90; flow-rate 35 ml min$^{-1}$; pressure 15 bar; retention time 87 min). MS (ISP): 228.4 ([M+H]$^+$). $[\alpha]_D^{20}$=−6.28° (c=0.52, methanol). 96% ee.

Example 48

(+)-4-(1H-Imidazol-4-ylmethyl)-3-methyl-3,4-dihydro-2H-benzo[1,4]oxazine

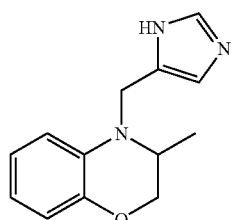

The enantiomers of (R,S)-4-(1H-imidazol-4-ylmethyl)-3-methyl-3,4-dihydro-2H-benzo[1,4]oxazine (Example 45) were separated with chiral HPLC (Chiracel OD column; eluant isopropanol/heptane 10:90; flow-rate 35 ml min$^{-1}$; pressure 15 bar; retention time 59 min). MS (ISP): 228.4 ([M+H]$^+$). $[\alpha]_D^{20}$=+31.8° (c=0.60, methanol).

Example 49

(−)-4-(1H-Imidazol-4-ylmethyl)-3-methyl-3,4-dihydro-2H-benzo[1,4]oxazine

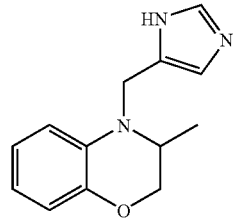

The enantiomers of (R,S)-4-(1H-imidazol-4-ylmethyl)-3-methyl-3,4-dihydro-2H-benzo[1,4]oxazine (Example 45) were separated with chiral HPLC (Chiracel OD column; eluant isopropanol/heptane 10:90; flow-rate 35 ml min$^{-1}$; pressure 15 bar; retention time 67 min). MS (ISP): 228.4 ([M+H]$^+$). $[\alpha]_D^{20}$=−24.4° (c=0.58, methanol). 76% ee.

Example 50

(R,S)-2-Ethyl-1-(1H-imidazol-4-ylmethyl)-1,2,3,4-tetrahydro-quinoline

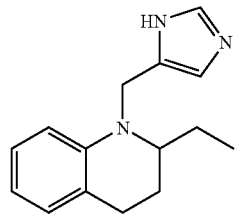

Analogously to Example 45, the title compound was obtained by reacting 3,4-dihydro-2(1H)-quinolinone and ethylmagnesium chloride in tetrahydrofuran, then treating the intermediate product with sodium borohydride in acetic acid and tetrahydrofuran, then treatment with imidazole-4-carboxaldehyde, sodium triacetoxyborohydride and acetic acid in 1,2-dichloroethane. MS (ISP): 242.3 ([M+H]$^+$).

Example 51

1-(3H-Imidazol-4-ylmethyl)-6-methoxy-1,2,3,4-tetrahydro-quinoline

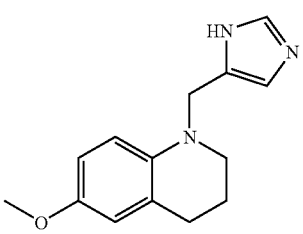

Analogously to Example 1, the title compound was obtained from 6-methoxy-1,2,3,4-tetrahydro-quinoline, imidazole-4-carboxaldehyde, sodium triacetoxyborohydride and acetic acid in 1,2-dichloroethane. MS (ISP): 244.4 ([M+H]$^+$).

Example 52

1-(3H-Imidazol-4-ylmethyl)-7-methoxy-1,2,3,4-tetrahydro-quinoline

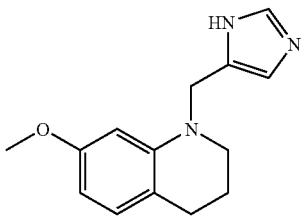

(a) 7-Hydroxy-3,4-dihydro-2H-quinoline-1-carboxylic acid tert-butyl ester

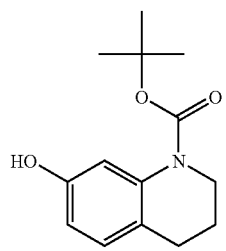

To a suspension of 1,2,3,4-tetrahydro-quinolin-7-ol (0.50 g, 3.35 mmol) in dichloromethane (40 ml) were added di-tert-butyldicarbonate (1.54 g, 7.04 mmol) and triethylamine (1.86 ml, 13.4 mmol) and the reaction mixture was stirred at 45° C. for 48 hours. The mixture was then acidified to pH 6 by addition of 10% aq. citric acid solution and extracted with dichloromethane. The combined organic phases were washed with saturated brine, dried over sodium sulphate, and concentrated in vacuo. The residue was dissolved in methanol (40 ml) and aq. sodium hydroxide solution (6.70 ml, 13.4 mmol, 2 M) was added. After stirring for 16 hours at 60° C., the mixture was cooled to room temperature and acidified to pH 6 by addition of 10% aq. citric acid solution and extracted with dichloromethane. The combined organic phases were dried over sodium sulphate and concentrated in vacuo to yield the title compound as a colorless oil which was used in the next step without further purification (0.33 g, 40%); MS (ISP): 250.3 ([M+H]$^+$), 194.4 ([M+H-Me$_2$C=CH$_2$]$^+$).

(b) 7-Methoxy-3,4-dihydro-2H-quinoline-1-carboxylic acid tert-butyl ester

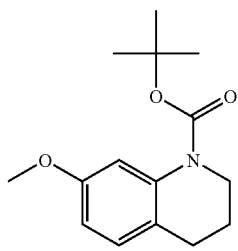

To a solution of 7-hydroxy-3,4-dihydro-2H-quinoline-1-carboxylic acid tert-butyl ester (120 mg, 0.48 mmol) in N,N-dimethylformamide (6 ml) was added sodium hydride (23 mg, 0.57 mmol, 60% dispersion in oil) and the reaction mixture was stirred at room temperature for 10 minutes. The mixture was then cooled to 0° C. and methyl iodide 0.04 ml, 0.64 mmol) was added dropwise. After stirring for 16 hours at room temperature, the mixture was quenched by addition of water (10 ml) and extracted three times with ethyl acetate. The combined organic phases were washed with saturated brine, dried over sodium sulphate, and concentrated in vacuo. The residue was purified by chromatography on silica gel (eluant: heptane/ethyl acetate gradient) to yield the title compound as a colorless oil (52 mg, 41%); MS (ISP): 264.0 ([M+H]$^+$), 208.1 ([M+H-Me$_2$C=CH$_2$]$^+$).

(c) 7-Methoxy-1,2,3,4-tetrahydro-quinoline

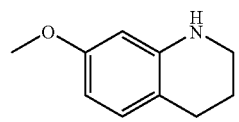

To a solution of 7-methoxy-3,4-dihydro-2H-quinoline-1-carboxylic acid tert-butyl ester (52 mg, 0.20 mmol) in dichloromethane (7 ml) at 0° C. was added dropwise trifluoroacetic acid (0.23 ml, 3.01 mmol) and the reaction mixture was then stirred at room temperature for 24 hours. The mixture was then made basic to pH 9 by dropwise addition of saturated aq. sodium carbonate solution. The mixture was extracted three times with a 1:1 mixture of ethyl acetate and tetrahydrofuran, the phases separated, and the organic phase dried over sodium sulphate and concentrated in vacuo to yield the title compound as a light brown oil (37 mg, 92%); MS (ISP): 164.4 ([M+H]$^+$).

(d) 1-(3H-Imidazol-4-ylmethyl)-7-methoxy-1,2,3,4-tetrahydro-quinoline

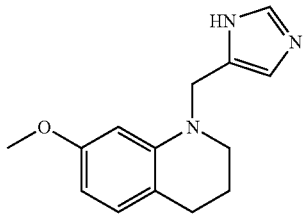

Analogously to Example 1, the title compound was obtained from 7-methoxy-1,2,3,4-tetrahydro-quinoline, imidazole-4-carboxaldehyde, sodium triacetoxyborohydride and acetic acid in 1,2-dichloroethane. MS (ISP): 244.4 ([M+H]$^+$).

Example 53

1-(1H-Imidazol-4-ylmethyl)-5-methoxy-1,2,3,4-tetrahydro-quinoline

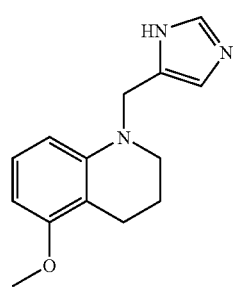

Analogously to Example 52, the title compound was obtained by reacting 1,2,3,4-tetrahydro-quinolin-5-ol, di-tert-butyldicarbonate and triethylamine in dichloromethane, then treating the resulting product with sodium hydroxide in methanol, then treating the product resulting therefrom with methyl iodide and sodium hydride in N,N-dimethylformamide, then treating the product resulting therefrom with trifluoroacetic acid, then treating the product resulting therefrom with imidazole-4-carboxaldehyde, sodium triacetoxyborohydride and acetic acid in 1,2-dichloroethane. MS (ISP): 244.4 ([M+H]$^+$).

Example 54

6-Benzyloxy-1-(1H-imidazol-4-ylmethyl)-1,2,3,4-tetrahydro-quinoline

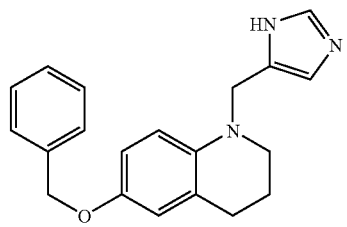

Analogously to Example 52, the title compound was obtained by reacting 1,2,3,4-tetrahydro-quinolin-6-ol, di-tert-butyldicarbonate and triethylamine in dichloromethane, then treating the resulting product with sodium hydroxide in methanol, then treating the product resulting therefrom with benzyl bromide and sodium hydride in N,N-dimethylformamide, then treating the product resulting therefrom with trifluoroacetic acid, then treating the product resulting therefrom with imidazole-4-carboxaldehyde, sodium triacetoxyborohydride and acetic acid in 1,2-dichloroethane. MS (ISP): 320.3 ([M+H]$^+$).

Example 55

5-Benzyloxy-1-(1H-imidazol-4-ylmethyl)-1,2,3,4-tetrahydro-quinoline

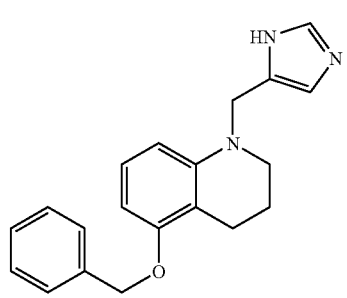

Analogously to Example 52, the title compound was obtained by reacting 1,2,3,4-tetrahydro-quinolin-5-ol, di-tert-butyldicarbonate and triethylamine in dichloromethane, then treating the resulting product with sodium hydroxide in methanol, then treating the product resulting therefrom with benzyl bromide and sodium hydride in N,N-dimethylformamide, then treating the product resulting therefrom with trifluoroacetic acid, then treating the product resulting therefrom with imidazole-4-carboxaldehyde, sodium triacetoxyborohydride and acetic acid in 1,2-dichloroethane. MS (ISP): 320.3 ([M+H]$^+$).

Example 56

1-(1H-Imidazol-4-ylmethyl)-5-isopropoxy-1,2,3,4-tetrahydro-quinoline

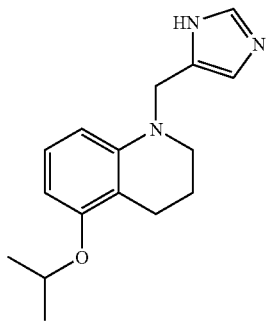

Analogously to Example 52, the title compound was obtained by reacting 1,2,3,4-tetrahydro-quinolin-5-ol, di-tert-butyldicarbonate and triethylamine in dichloromethane, then treating the product resulting therefrom with sodium hydroxide in methanol, then treating the product resulting therefrom with isopropyl bromide and sodium hydride in N,N-dimethylformamide, then treating the product resulting therefrom with trifluoroacetic acid, then treating the product resulting therefrom with imidazole-4-carboxaldehyde, sodium triacetoxyborohydride and acetic acid in 1,2-dichloroethane. MS (ISP): 272.3 ([M+H]$^+$).

Example 57

7-Benzyloxy-1-(1H-imidazol-4-ylmethyl)-1,2,3,4-tetrahydro-quinoline

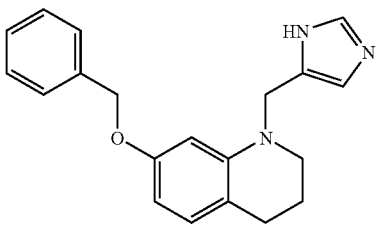

Analogously to Example 52, the title compound was obtained by reacting 1,2,3,4-tetrahydro-quinolin-7-ol, di-tert-butyldicarbonate and triethylamine in dichloromethane, then treating the resulting product with sodium hydroxide in methanol, then treating the product resulting therefrom with benzyl bromide and sodium hydride in N,N-dimethylformamide, then treating the product resulting therefrom with trifluoroacetic acid, then treating the product resulting therefrom with imidazole-4-carboxaldehyde, sodium triacetoxyborohydride and acetic acid in 1,2-dichloroethane. MS (ISP): 320.3 ([M+H]$^+$).

Example 58

7-Ethoxy-1-(1H-imidazol-4-ylmethyl)-1,2,3,4-tetrahydro-quinoline

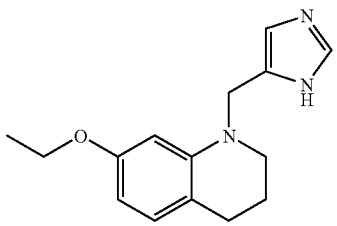

Analogously to Example 52, the title compound was obtained by reacting 1,2,3,4-tetrahydro-quinolin-7-ol, di-tert-butyldicarbonate and triethylamine in dichloromethane, then treating the resulting product with sodium hydroxide in methanol, then treating the product resulting therefrom with iodoethane and sodium hydride in N,N-dimethylformamide, then treating the product resulting therefrom with trifluoroacetic acid, then treating the product resulting therefrom with imidazole-4-carboxaldehyde, sodium triacetoxyborohydride and acetic acid in 1,2-dichloroethane. MS (ISP): 258.0 ([M+H]$^+$).

Example 59

1-(1H-Imidazol-4-ylmethyl)-7-isopropoxy-1,2,3,4-tetrahydro-quinoline

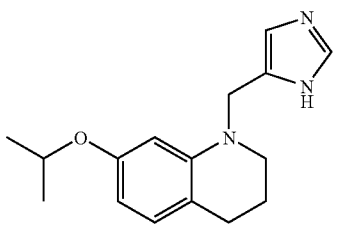

Analogously to Example 52, the title compound was obtained by reacting 1,2,3,4-tetrahydro-quinolin-7-ol, di-tert-butyldicarbonate and triethylamine in dichloromethane, then treating the resulting product with sodium hydroxide in methanol, then treating the product resulting therefrom with 2-bromopropane and sodium hydride in N,N-dimethylformamide, then treating the product resulting therefrom with trifluoroacetic acid, then treating the product resulting therefrom with imidazole-4-carboxaldehyde, sodium triacetoxyborohydride and acetic acid in 1,2-dichloroethane. MS (ISP): 272.5 ([M+H]$^+$).

Example 60

1-(1H-Imidazol-4-ylmethyl)-7-phenoxy-1,2,3,4-tetrahydro-quinoline

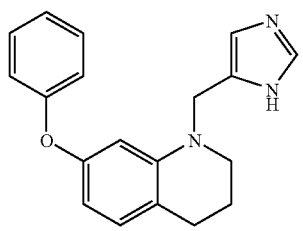

(a) 7-Phenoxy-1,2,3,4-tetrahydro-quinoline

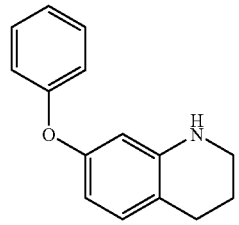

To a solution of 0.15 g (1.01 mmol) 1,2,3,4-tetrahydro-quinolin-7-ol in 10 ml dichloromethane were added 0.19 g (1.56 mmol) phenylboronic acid, 0.27 g (1.49 mmol) copper (II) acetate, a spatula end of 4 Å molecular sieves and 0.64 ml (5.03 mmol) triethylamine. The reaction mixture was stirred at room temperature for 72 hours and then filtered through celite, washing with dichloromethane. The filtrate was concentrated in vacuo and the residue was purified by flash chromatography (silica gel, ethyl acetate/heptane gradient) to afford 15 mg (7%) of the title compound as a light yellow oil. MS (ISP): 226.3 ([M+H]$^+$).

(b) 1-(1H-Imidazol-4-ylmethyl)-7-phenoxy-1,2,3,4-tetrahydro-quinoline

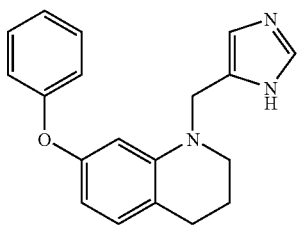

Analogously to Example 1, the title compound was obtained from 7-phenoxy-1,2,3,4-tetrahydro-quinoline, imidazole-4-carboxaldehyde, sodium triacetoxyborohydride and acetic acid in 1,2-dichloroethane. MS (ISP): 306.4 ([M+H]$^+$).

Example 61

1-(1H-Imidazol-4-ylmethyl)-5-phenoxy-1,2,3,4-tetrahydro-quinoline

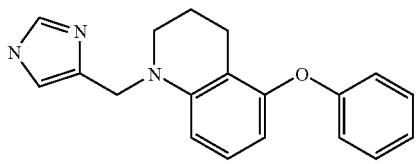

Analogously to Example 60, the title compound was obtained by reacting 1,2,3,4-tetrahydro-quinolin-5-ol, phenylboronic acid, copper(II) acetate and triethylamine in dichloromethane, then treating the intermediate compound with imidazole-4-carboxaldehyde, sodium triacetoxyborohydride and acetic acid in 1,2-dichloroethane. MS (ISP): 306.1 ([M+H]$^+$).

Example 62

The ability of the compounds of the present invention to bind to TAAR1 was demonstrated in accordance with the test given hereinafter.

Materials and Methods

Construction of TAAR Expression Plasmids and Stably Transfected Cell Lines

For the construction of expression plasmids, the coding sequences of human, rat and mouse TAAR 1 were amplified from genomic DNA essentially as described by Lindemann et al. (2005) *Genomics* 85, 372-385. The Expand High Fidelity PCR System (Roche Diagnostics) was used with 1.5 mM $Mg^{2+}$ and purified PCR products were cloned into pCR2.1-TOPO cloning vector (Invitrogen) following the instructions of the manufacturer. PCR products were subcloned into the pIRESneo2 vector (BD Clontech, Palo Alto, Calif.), and expression vectors were sequence verified before introduction in cell lines.

HEK293 cells (ATCC # CRL-1573) were cultured essentially as described in Lindemann et al. (2005) *Genomics* 85, 372-385. For the generation of stably transfected cell lines, HEK293 cells were transfected with the pIRESneo2 expression plasmids containing the TAAR coding sequences (described above) with Lipofectamine 2000 (Invitrogen) according to the instructions of the manufacturer, and 24 hours post transfection, the culture medium was supplemented with 1 mg/ml G418 (Sigma, Buchs, Switzerland). After a culture period of about 10 days, clones were isolated, expanded and tested for responsiveness to trace amines (all compounds purchased from Sigma) with the cAMP Biotrak Enzyme immunoassay (EIA) System (Amersham) following the non-acetylation EIA procedure provided by the manufacturer. Monoclonal cell lines which displayed a stable $EC_{50}$ for a culture period of 15 passages were used for all subsequent studies.

Membrane Preparation and Radioligand Binding

Cells at confluence were rinsed with ice-cold phosphate buffered saline without $Ca^{2+}$ and $Mg^{2+}$ containing 10 mM EDTA and pelleted by centrifugation at 1000 rpm for 5 minutes at 4° C. The pellet was then washed twice with ice-cold phosphate buffered saline and the cell pellet was frozen immediately by immersion in liquid nitrogen and stored until use at −80° C. The cell pellet was then suspended in 20 ml HEPES-NaOH (20 mM), pH 7.4 containing 10 mM EDTA, and homogenized with a Polytron (PT 3000, Kinematica) at 10,000 rpm for 10 seconds. The homogenate was centrifuged at 48,000×g for 30 minutes at 4° C. and the pellet resuspended in 20 ml HEPES-NaOH (20 mM), pH 7.4 containing 0.1 mM EDTA (buffer A), and homogenized with a Polytron at 10,000 rpm for 10 seconds. The homogenate was then centrifuged at 48,000×g for 30 minutes at 4° C. and the pellet resuspended in 20 ml buffer A, and homogenized with a Polytron at 10,000 rpm for 10 seconds. Protein concentration was determined by the method of Pierce (Rockford, Ill.). The homogenate was then centrifuged at 48,000×g for 10 minutes at 4° C., resuspended in HEPES-NaOH (20 mM), pH 7.0 including $MgCl_2$ (10 mM) and $CaCl_2$ (2 ml) (buffer B) at 200 μg protein per ml and homogenized with a Polytron at 10,000 rpm for 10 seconds.

Binding assay was performed at 4° C. in a final volume of 1 ml, and with an incubation time of 30 minutes. The radioligand [$^3$H]-rac-2-(1,2,3,4-tetrahydro-1-naphthyl)-2-imidazoline was used at a concentration equal to the calculated $K_d$ value of 60 nM to give a total binding at around 0.1% of the total added radioligand concentration, and a specific binding which represented approximately 70-80% of the total binding. Non-specific binding was defined as the amount of [$^3$H]-rac-2-(1,2,3,4-tetrahydro-1-naphthyl)-2-imidazoline bound in the presence of the appropriate unlabelled ligand (10 μM). Competing ligands were tested in a wide range of concentrations (10 pM-30 μM). The final dimethylsulphoxide concentration in the assay was 2%, and it did not affect radioligand binding. Each experiment was performed in duplicate. All incubations were terminated by rapid filtration through Uni-Filter-96 plates (Packard Instrument Company) and glass filter GF/C) pre-soaked for at least 2 hours in polyethylenimine 0.3%, and using a Filtermate 96 Cell Harvester (Packard Instrument Company). The tubes and filters were then washed 3 times with 1 ml aliquots of cold buffer B. Filters were not dried and soaked in Ultima gold (45 μl/well, Packard Instrument Company) and bound radioactivity was counted by a TopCount Microplate Scintillation Counter (Packard Instrument Company).

The preferred compounds show a Ki value (μM) in mouse on TAAR1 in the range of 0.001-0.100 as shown in the table below.

| Compound of Example | Ki (μM) mouse | Compound of Example | Ki | Compound of Example | Ki |
|---|---|---|---|---|---|
| 1 | 0.0688 | 27 | 0.0389 | 40 | 0.0405 |
| 2 | 0.0104 | 28 | 0.0409 | 41 | 0.0104 |
| 3 | 0.0258 | 29 | 0.0115 | 43 | 0.0538 |
| 4 | 0.0091 | 31 | 0.0243 | 44 | 0.0151 |
| 6 | 0.0598 | 32 | 0.0403 | 45 | 0.017 |
| 7 | 0.0264 | 33 | 0.003 | 47 | 0.0872 |
| 14 | 0.0102 | 34 | 0.0133 | 49 | 0.0573 |
| 16 | 0.0345 | 35 | 0.0323 | 55 | 0.0046 |
| 18 | 0.0578 | 36 | 0.0277 | 57 | 0.0702 |
| 23 | 0.0042 | 37 | 0.0106 | 61 | 0.0027 |
| 25 | 0.0016 | 38 | 0.0144 | | |
| 26 | 0.0834 | 39 | 0.0493 | | |

Example 63

Tablet Formulation (Wet Granulation)

| | | mg/tablet | | | |
|---|---|---|---|---|---|
| Item | Ingredients | 5 mg | 25 mg | 100 mg | 500 mg |
| 1. | Compound of formula I | 5 | 25 | 100 | 500 |
| 2. | Lactose Anhydrous DTG | 125 | 105 | 30 | 150 |
| 3. | Sta-Rx 1500 | 6 | 6 | 6 | 30 |
| 4. | Microcrystalline Cellulose | 30 | 30 | 30 | 150 |
| 5. | Magnesium Stearate | 1 | 1 | 1 | 1 |
| | Total | 167 | 167 | 167 | 831 |

Manufacturing Procedure
1. Mix items 1, 2, 3 and 4 and granulate with purified water.
2. Dry the granules at 50° C.
3. Pass the granules through suitable milling equipment.
4. Add item 5 and mix for three minutes; compress on a suitable press.

Example 64

Capsule Formulation

| | | mg/capsule | | | |
|---|---|---|---|---|---|
| Item | Ingredients | 5 mg | 25 mg | 100 mg | 500 mg |
| 1. | Compound of formula I | 5 | 5 | 100 | 500 |
| 2. | Hydrous Lactose | 159 | 123 | 148 | — |
| 3. | Corn Starch | 25 | 35 | 40 | 70 |

-continued

Capsule Formulation

| Item | Ingredients | 5 mg | 25 mg | 100 mg | 500 mg |
|---|---|---|---|---|---|
| | | \multicolumn{4}{c}{mg/capsule} | | | |
| 4. | Talc | 10 | 15 | 10 | 25 |
| 5. | Magnesium Stearate | 1 | 2 | 2 | 5 |
| | Total | 200 | 200 | 300 | 600 |

Manufacturing Procedure
1. Mix items 1, 2 and 3 in a suitable mixer for 30 minutes.
2. Add items 4 and 5 and mix for 3 minutes.
3. Fill into a suitable capsule.

The invention claimed is:
1. A compound of formula I,

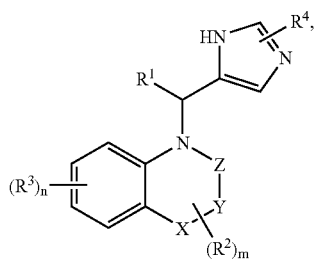

wherein
$R^1$ is selected from the group consisting of hydrogen and lower alkyl;
each $R^2$ is independently selected from the group consisting of hydrogen and lower alkyl;
each $R^3$ is independently selected from the group consisting of lower alkoxy, phenyloxy, and benzyloxy;
$R^4$ is selected from the group consisting of hydrogen and lower alkyl;
X is selected from the group consisting of —CH$_2$—, —CH— and —O—;
Y is selected from the group consisting of —CH$_2$—, —CH$_2$CH$_2$—, and a bond; with the proviso that, when X is —O—, Y is —CH$_2$—;
Z is selected from the group consisting of —CH$_2$— and —CH—;
m is 1 or 2; and
n is 1 or 2;
or a pharmaceutically-acceptable acid-addition salt thereof.
2. A compound according to claim 1, wherein X is —CH$_2$— and Y is a bond.
3. A compound according to claim 2, selected from the group consisting of:
   1-(1H-imidazol-4-ylmethyl)-5-methoxy-2,3-dihydro-1H-indole;
   1-(1H-imidazol-4-ylmethyl)-6-methoxy-2,3-dihydro-1H-indole;
   1-(1H-imidazol-4-ylmethyl)-7-methoxy-2,3-dihydro-1H-indole;
   1-(1H-imidazol-4-ylmethyl)-4-methoxy-2,3-dihydro-1H-indole; and
pharmaceutically-acceptable acid-addition salts thereof.
4. A compound according to claim 2, selected from the group consisting of:
   (R,S)-1-(1H-Imidazol-4-ylmethyl)-5-methoxy-2-methyl-2,3-dihydro-1H-indole; and pharmaceutically-acceptable acid-addition salts thereof.
5. A compound according to claim 1, wherein X is —CH$_2$— and Y is —CH$_2$—.
6. A compound according to claim 5, selected from the group consisting of:
   5-benzyloxy-1-(1H-imidazol-4-ylmethyl)-1,2,3,4-tetrahydro-quinoline;
   7-benzyloxy-1-(1H-imidazol-4-ylmethyl)-1,2,3,4-tetrahydro-quinoline;
   1-(1H-imidazol-4-ylmethyl)-5-phenoxy-1,2,3,4-tetrahydro-quinoline; and
pharmaceutically-acceptable acid-addition salts thereof.
7. A compound according to claim 5, selected from the group consisting of:
   1-(3H-Imidazol-4-ylmethyl)-6-methoxy-1,2,3,4-tetrahydro-quinoline;
   1-(3H-Imidazol-4-ylmethyl)-7-methoxy-1,2,3,4-tetrahydro-quinoline;
   1-(1H-Imidazol-4-ylmethyl)-5-methoxy-1,2,3,4-tetrahydro-quinoline;
   6-Benzyloxy-1-(1H-imidazol-4-ylmethyl)-1,2,3,4-tetrahydro-quinoline;
   1-(1H-Imidazol-4-ylmethyl)-5-isopropoxy-1,2,3,4-tetrahydro-quinoline;
   7-Ethoxy-1-(1H-imidazol-4-ylmethyl)-1,2,3,4-tetrahydro-quinoline;
   1-(1H-Imidazol-4-ylmethyl)-7-isopropoxy-1,2,3,4-tetrahydro-quinoline; 1-(1H-Imidazol-4-ylmethyl)-7-phenoxy-1,2,3,4-tetrahydro-quinoline; and
pharmaceutically-acceptable acid-addition salts thereof.
8. A compound according to claim 1, wherein X is O and Y is —CH$_2$—.
9. A compound according to claim 1, wherein X is —CH$_2$— and Y is —CH$_2$CH$_2$—.
10. A compound according to claim 9, which is
   1-(3H-imidazol-4-ylmethyl)-7-methoxy-2,3,4,5-tetrahydro-1H-benzo[b]azepine;
or a pharmaceutically-acceptable acid-addition salt thereof.
11. A process for the preparation of a compound of formula I,

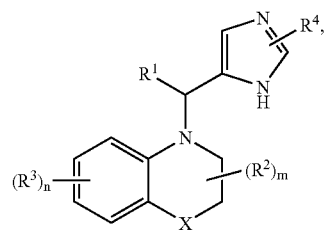

comprising reductively aminating a compound of formula II,

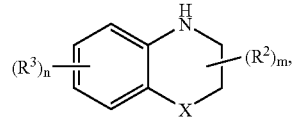

and a compound of formula III,

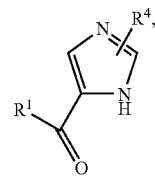

wherein, in the aforementioned formulas,
- R¹ is selected from the group consisting of hydrogen and lower alkyl;
- each R² is independently selected from the group consisting of hydrogen and lower alkyl;
- each R³ is independently selected from the group consisting of lower alkoxy, phenyloxy, and benzyloxy;
- R⁴ is selected from the group consisting of hydrogen and lower alkyl;
- X is selected from the group consisting of —CH$_2$—, —CH— and —O—;
- m is 1 or 2; and
- n is 1 or 2.

12. A composition comprising a compound of formula I,

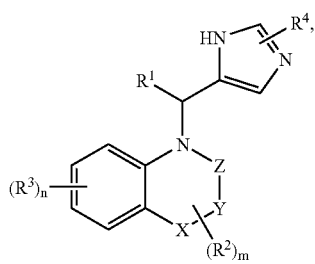

I wherein
- R¹ is selected from the group consisting of hydrogen and lower alkyl;
- each R² is independently selected from the group consisting of hydrogen and lower alkyl;
- each R³ is independently selected from the group consisting of lower alkoxy, phenyloxy, and benzyloxy;
- R⁴ is selected from the group consisting of hydrogen and lower alkyl;
- X is selected from the group consisting of —CH$_2$—, —CH— and —O—;
- Y is selected from the group consisting of —CH$_2$—, —CH$_2$CH$_2$—, —CH— and a bond; with the proviso that, when X is —O—, Y is —CH$_2$—;
- Z is selected from the group consisting of —CH$_2$— and —CH—.
- m is 1 or 2; and
- n is 1 or 2;

or a pharmaceutically-acceptable acid-addition salt thereof, and therapeutically-inert carrier.

* * * * *